(12) United States Patent
Bachovchin

(10) Patent No.: US 7,727,964 B2
(45) Date of Patent: *Jun. 1, 2010

(54) PEPTIDOMIMETIC INHIBITORS OF POST-PROLINE CLEAVING ENZYMES

(75) Inventor: William W. Bachovchin, Melrose, MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/496,706

(22) PCT Filed: Nov. 26, 2002

(86) PCT No.: PCT/US02/38053

§ 371 (c)(1),
(2), (4) Date: Oct. 22, 2004

(87) PCT Pub. No.: WO03/045977

PCT Pub. Date: Jun. 5, 2003

(65) Prior Publication Data

US 2005/0070482 A1    Mar. 31, 2005

Related U.S. Application Data

(60) Provisional application No. 60/405,530, filed on Aug. 23, 2002, provisional application No. 60/333,519, filed on Nov. 26, 2001.

(51) Int. Cl.
| | |
|---|---|
| A61K 38/05 | (2006.01) |
| A61K 31/195 | (2006.01) |
| A61K 31/69 | (2006.01) |
| C07K 5/065 | (2006.01) |
| C07K 5/068 | (2006.01) |
| C07K 5/072 | (2006.01) |
| C07K 5/06 | (2006.01) |
| C07C 233/00 | (2006.01) |
| C07C 235/00 | (2006.01) |
| C07C 237/00 | (2006.01) |
| C07C 231/00 | (2006.01) |
| C07C 231/02 | (2006.01) |
| C07C 231/08 | (2006.01) |

(52) U.S. Cl. ............................ 514/19; 514/2; 514/64; 514/563

(58) Field of Classification Search ............ None
See application file for complete search history.

(56) References Cited

U.S. PATENT DOCUMENTS

| | | | |
|---|---|---|---|
| 4,499,082 A * | 2/1985 | Shenvi et al. ............ | 514/2 |
| 4,522,752 A | 6/1985 | Sisto et al. | |
| 4,698,327 A * | 10/1987 | Nagarajan et al. ........ | 514/8 |
| 4,935,493 A | 6/1990 | Bachovchin et al. | |
| 4,963,655 A * | 10/1990 | Kinder et al. ............ | 530/331 |
| 5,061,811 A | 10/1991 | Pinori et al. | |
| 5,462,928 A | 10/1995 | Bachovchin et al. | |
| 5,463,124 A * | 10/1995 | Jacobi et al. ............. | 564/155 |
| 5,543,396 A | 8/1996 | Powers et al. | |
| 5,574,017 A * | 11/1996 | Gutheil .................... | 514/19 |
| 5,580,979 A | 12/1996 | Bachovchin | |
| 5,585,390 A | 12/1996 | Duflos et al. | |
| 5,631,224 A | 5/1997 | Efendic et al. | |
| 5,679,782 A * | 10/1997 | Rosenberg et al. ....... | 536/23.1 |
| 5,721,214 A * | 2/1998 | Marlowe et al. .......... | 514/18 |
| 5,776,902 A | 7/1998 | Bachovchin | |
| 5,783,556 A | 7/1998 | Clark et al. | |
| 5,834,428 A | 11/1998 | Drucker | |
| 5,952,301 A | 9/1999 | Drucker | |
| 5,965,532 A | 10/1999 | Bachovchin | |
| 6,011,155 A | 1/2000 | Villhauer | |
| 6,258,597 B1 | 7/2001 | Bachovchin et al. | |
| 6,300,314 B1 | 10/2001 | Wallner et al. | |
| 6,355,614 B1 | 3/2002 | Wallner | |
| 6,703,238 B2 | 3/2004 | Bachovchin et al. | |
| 6,770,628 B2 | 8/2004 | Wallner et al. | |
| 6,803,357 B1 | 10/2004 | Bachovchin et al. | |
| 6,825,169 B1 | 11/2004 | Bachovchin et al. | |
| 6,890,898 B2 | 5/2005 | Bachovchin et al. | |
| 6,890,904 B1 | 5/2005 | Wallner et al. | |
| 6,949,514 B2 | 9/2005 | Wallner et al. | |

(Continued)

FOREIGN PATENT DOCUMENTS

WO    WO-89/03223    4/1989

(Continued)

OTHER PUBLICATIONS

E. Swain, ed. Pharm. Med. Pack. News Aug. 1999, 4 pages.*

(Continued)

*Primary Examiner*—Andrew D Kosar
(74) *Attorney, Agent, or Firm*—Dana M. Gordon; Foley Hoag LLP

(57) ABSTRACT

The present invention relates to inhibitors of post-proline cleaving enzymes, such as inhibitors of dipeptidyl peptidase IV, as well as pharmaceutical compositions thereof, and methods for using such inhibitors. In particular, the inhibitors of the present invention are improved over those in the prior art by selection of particular classes of sidechains in the P1 and/or P2 position of the inhibitor. The compounds of the present invention can have a better therapeutic index, owing in part to reduced toxicity and/or improved specificity for the targeted protease.

6 Claims, 23 Drawing Sheets

U.S. PATENT DOCUMENTS

| | | | |
|---|---|---|---|
| 6,979,697 | B1 | 12/2005 | Wallner |
| 2001/0020006 | A1* | 9/2001 | Demuth et al. ................ 514/19 |
| 2003/0045228 | A1* | 3/2003 | Johnson ...................... 454/343 |
| 2003/0153509 | A1 | 8/2003 | Bachovchin et al. |
| 2003/0158114 | A1 | 8/2003 | Wallner et al. |
| 2004/0077601 | A1 | 4/2004 | Adams et al. |
| 2004/0152192 | A1 | 8/2004 | Bachovchin et al. |
| 2004/0176307 | A1 | 9/2004 | Bachovchin et al. |
| 2004/0229820 | A1 | 11/2004 | Bachovchin et al. |
| 2005/0037976 | A1 | 2/2005 | Wallner et al. |
| 2005/0049177 | A1 | 3/2005 | Bachovchin et al. |
| 2005/0070482 | A1 | 3/2005 | Bachovchin |
| 2005/0084490 | A1 | 4/2005 | Adams et al. |
| 2005/0203027 | A1 | 9/2005 | Bachovchin et al. |
| 2005/0272703 | A1 | 12/2005 | Wallner et al. |
| 2006/0052310 | A1 | 3/2006 | Wallner |
| 2006/0063719 | A1 | 3/2006 | Jesson et al. |

FOREIGN PATENT DOCUMENTS

| | | |
|---|---|---|
| WO | WO-93/08259 | 4/1993 |
| WO | WO 95/11689 | 5/1995 |
| WO | WO-95/15309 | 6/1995 |
| WO | WO 95/29691 | 11/1995 |
| WO | WO 95/34538 | 12/1995 |
| WO | WO-96/14857 | 5/1996 |
| WO | WO-96/39385 A1 | 12/1996 |
| WO | WO-97/40832 | 11/1997 |
| WO | WO-98/19998 | 5/1998 |
| WO | WO-98/25644 | 6/1998 |
| WO | WO 98/50046 | 11/1998 |
| WO | WO 99/38501 | 8/1999 |
| WO | WO9967279 A1 * | 12/1999 |
| WO | WO-00/10549 | 3/2000 |
| WO | WO 00/55126 | 9/2000 |
| WO | WO 00/61789 | 10/2000 |
| WO | WO 00/71135 A1 | 11/2000 |
| WO | WO-01/14318 A2 | 3/2001 |
| WO | WO 01/27138 A2 | 4/2001 |
| WO | WO-01/34594 | 5/2001 |
| WO | WO-01/81337 | 11/2001 |
| WO | WO 03/033524 A2 | 4/2003 |
| WO | WO 03/045228 A2 | 6/2003 |
| WO | WO 03/092605 A2 | 11/2003 |

OTHER PUBLICATIONS

S. Rudikoff, et al. Proc. Natl. Acad. Sci. USA (1982) 79, pp. 1979-1983.*

W.S. Messer, "Vasopressin and Oxytocin", web document updated Apr. 3, 2000; <http://www.neurosci.pharm.utoledo.edu/MBC3320/vasopressin.htm>; 5 pages.*

D.E. Smilek, et al. Proc. Natl. Acad. Sci. USA (1991) 88, pp. 9633-9637.*

J. Rudinger. In: Peptide Hormones, JA Parsons, Ed. (1976) 1-7.*

C. Southan. FEBS Letters (2001) 498, pp. 214-218.*

A. Lupas, et al. TIBS (1997) 22, p. 399-404.*

L.B. Pena, et al. Elect. J. Biotech. (2006) 9(3), pp. 258-262.*

C.A. Kettner and A.B. Shenvi. J. Biol. Chem. (1984) 259(24), pp. 15106-15114.*

Bell et al., 1983, "Exon duplication and divergence in the human preproglucagon gene", Nature 304 (5924):368-71.

Conlon, 1988, "Proglucagon-derived peptides: nomenclature, biosynthetic relationships and physiological roles", Diabetolgia 31(8):536-6.

Coutts et al. Structure-Activity Relationships of Boronic Acid Inhibitors of Dipeptidyl Peptidase IV. I. Variation of the P2 Position of Xaa-boroPro Dipeptides. J. Med. Chem. 39, 2087-2094 (1996).

Deacon et al. Degradation of Glucagon-Like Peptide-1 by Human Plasma in Vitro Yields an N-Terminally Truncated Peptide that is a Major Endogenous Metabolite in Vivo. J. Clin. Endocrin. 83, 952-957 (1995).

Gutniak et al., 1992, "Antidiabetogenic effect of glucagon-like peptide-1 (7-36) amide in normal subjects and patients with diabetes mellitus", N Engl J Med 326(20):1316-22.

Holst, J. J. & Deacon, C.F. Inhibition of the Activity of Dipeptidyl-Peptidase IV as a Treatment for Type 2 Diabetes. Diabetes 47, 1663-1670 (1998).

Kawashima et al., 1990, "Pharmacological differentiation of presynaptic M1 muscarinic receptors modulating acetylcholine release from postsynaptic muscarinic receptors in guinea-pig ileum", Gen Pharmacol 21(1):17-21.

Kinder et al., 1985, "Acylamino boronic acids and difluoroborane analogues of amino acids: potent inhibitors of chymotrypsin and elastase", J Med Chem 28(12):1917-25.

Kubiak et al., 1994, "Metabolism or mouse growth hormone-releasing factor, mGRF(1-42)OH, and selected analogs from the bovine GRF series in mouse and bovine plasma in vitro", Pept Res 7(3):153-61.

Lund et al., 1982, "Pancreatic preproglucagon cDNA contains two glucagon-related coding sequences arranged in tandem", Proc Natl Acad Sci U S A 79(2):345-9.

Mentlein et al. Dipeptidyl-peptidase IV hydrolyses gastric inhibitory polypeptide, glucagons-like peptide-1(7-36)amide, peptide histidine methionine and is responsible for their degradation in human serum. Eur. J. Biochem. 214, 829-835 (1993).

Mojsov et al., 1986, "Preproglucagon gene expression in pancreas and intestine diversifies at the level of post-translational processing", J Biol Chem 261(25):11880-9.

Mojsov, 1992, "Structural requirements for biological activity of glucagon-like peptide-1", Int J Pept Protein Res 40(3-4):333-43.

Patzelt et al., 1979, "Identification and processing of proglucagon in pancreatic islets", Nature 282(5736):260-6.

Pospisilik, John A. et al. Metabolism of Glucagon by Dipeptidyl Peptidase IV (CD26). Regulatory Peptides 96, 133-141.

Schmidt et al., 1985, "Glucagon-like peptide-1 but not glucagon-like peptide-2 stimulates insulin release from isolated rat pancreatic islets", Diabetologia 28(9):704-7.

Stanely et al., 1989, "Repeated hypothalamic stimulation with neuropeptide Y increases daily carbohydrate and fat intake and body weight gain in female rats", Physiol Behav 46(2):173-7.

Wilding et al., 1992, "Increased neuropeptide Y content in individual hypothalamic nuclei, but not neuropeptide Y mRNA, in diet-induced obesity in rats", J Endocrinol 132(2):299-304.

Dupre, 1991, "Influences of the gut on the endocrine pancreas" The Endocrine Pancreas (Raven Press, New York) pp. 253-281.

Weir et al., 1989, "Glucagonlike peptide I (7-37) actions on endocrine pancrease", Diabetes 38(3):338-42.

Shue et al., 1987, "Amide bond surrogates: a general synthetic route to trans carbon-carbon double bond isosteres", Tetrahedron Letters 28:3225.

Radhakrishna et al., 1979, "New method for direct conversion of amides to amines", J Org Chem 44:1746.

Pederson et al. Improved Glucose Tolerance in Zucker Fatty Rats by Oral Administration of the Dipeptidyl Peptidase IV Inhibitor Isoleucine Thiazolidide. Diabetes 47, 1253-1258 (Aug. 1998).

Orskov et al., 1987, "Pancreatic and intestinal processing of proglucagon in man," Diabetologia 30(11):874-81.

Mojsov et al., 1987, "Insulinotropin: glucagon-like peptide I (7-37) co-encoded in the glucagon gene is a potent stimulator of insulin release in the perfused rat pancreas", J Clin Invest 79(2):616-9.

Mentlein et al. Proteolytic processing of neuropeptide Y and peptide YY by dipeptidyl peptidase IV. Regulatory Peptides 49, 133-144 (Dec. 10, 1993).

Matteson et al., 1984, "Synthesis and properties of pinanediol A-amino boronic acids", Organometallics 3:1284.

Lambrecht et al., 1989, "Pharmacology of hexahydro-difenidol, hexahydro-sila-difenidol and related selective muscarinic antagonists", Trends Pharmacol Sci 10(Suppl):60.

Kreymann et al., 1987, "Glucagon-like peptide-1 7-36: a physiological incretin in man", Lancet 2(8571):1300-4.

Kieffer et al. Degradation of Glucose-Dependent Insulinotropic Polypeptide and Truncated Glucagon-Like Peptide 1 in Vitro and in Vivo by Dipeptidyl Peptidase IV, Endocrin. 136, 3585-3596 (1995).

Holst et al., 1987, "Truncated glucagon-like peptide I, an insulin-releasing hormone from the distal gut", FEBS Lett. 211(2):169-74.

Habener et al., 1991, "Biosyntesies of glucagon" The Endocrine Pancreas (Raven Press, New York) pp. 53-71.

Ebert et al., 1987, "Gastrointestinal peptides and insulin secretion", Diabetes Met. Rev. 3:1-26.

Deacon et al., 1995, "Both subcutaneously and intravenously administered glucagon-like peptide I are rapidly degraded from the NH2-terminus in type II diabetic patients and in healthy subjects", Diabetes 44(9):1126-31.

Coruzzi et al., 1989, "Gastric antisecretory activity of telenzepine, a new MI-selective muscarinic antagonist: comparison with pirenzepine", Arch Int Pharmacodyn Ther 302:232-41.

Bell et al., 1983, "Hamster preproglucagon contains the sequence of glucagon and two related peptides", Nature 302(5910):716-8.

Balkan et al. Improved insulin secretion and oral glucose tolerance after in vivo inhibition of DPP-IV in obese zucker rats. Diabetolgia Suppl. 40, A131 Abstract (1997).

Deacon et al. Diabetes. 1998. vol. 47, pp. 764-769.

Jolles et al., Pristinamycin, Bull. Soc. Chim France (1965) 8, 2252-9 Chemical Abstracts 63:72425 See the structure in the abstract.

Bachovchin, W. W. et al., "Inhibition of IgAl Proteinases from *Neisseria gonorrhoeae* and *Hemophilus influenzae* by Peptide Prolyl Boronic Acids", *Journ. of Biol. Chem.*, 265(7):37383743 (Mar. 5, 1990).

Coutts, S. J. et al., "Structure-Activity Relationships of Boronic Acid Inhibitors of Dpeptidyl Peptidase IV. 1. Variation of the $P_2$ Position of $X_{aa}$-boroPro Dipeptides", *Journ. of Med. Chem.*, 39(39):2087-2094 (May 10, 1996).

Flentke, G. R. et al., "Inhibition of dipeptidyl aminopeptidase IV (DP-IV) by Xaa-boroPro dipeptides and use of these inhibitors to examiner the role of DP-IV in T-cell function", *Proc. Natl. Acad. Sci. USA*, 88:1556-1559 (Feb. 1991).

Lambier, A-M. et al., "Dipeptide-derived diphenyl phosphonate esters: mechanism-based inhibitors of dipeptidyl peptidase IV", *Biochimica et Biophiysica Acta*, 1290(1):76-82 (May 21, 1996).

Pargellis, C. A. et al., "Inhibition of Dpeptidyl Peptidase IV (CD26) by Peptide Boronic Acid Dipeptides", *J. Enzyme Inhibition*, 11:151-169 (1997).

Snow, R. J. et al., "Studies on Proline Boronic Acid Dipeptide Inhibitors of Dipeptidyl Peptidase IV: Identification of a Cyclic Species Containing a B-N. Bond", J. Am. Chem. Soc., 116(24):10860-10869(1994).

Supplementary Partial European Search Report dated Mar.30, 2007.

Loidl, G. et al., "Bifunctional inhibitors of the trypsin-like activity of eukaryotic proteasomes", *Chemistry & Biology*, 6:194-204 (Elsevier Science Ltd.)(Apr. 1999).

Ogilvie, W. et al., "Peptidomimetic Inhibitors of the Human Cytomegalovirus Protease", *J. Med. Chem.*, 40:4113-4135 (American Chemical Society)(1997).

* cited by examiner

Sythesis Of Cyclohexylglycine boroAla

Blood Glucose Values (mmol/L) During Oral Glucose Challenge Test in Zucker Rats Following Oral Administration of Cyclohexylglycine-Alanine Boronic Acid Conformational Equilibrium of Xaa-boro-Alanine Inhibitors open chain form            cyclic form

PEPTIDOMIMETIC INHIBITORS OF POST-PROLINE CLEAVING ENZYMES

CROSS-REFERENCE TO RELATED APPLICATIONS

This application is a national stage filing under 35 U.S.C. 371 of International Application PCT/US02/38053, filed Nov. 26, 2002, which claims priority from U.S. Application No. 60/333,519 filed Nov. 26, 2001, and U.S. Application No. 60/405,530 filed Aug. 23, 2002, the specifications of each of which are hereby incorporated by reference in their entirety. International Application PCT/US02/38053 was published under PCT Article 21(2) in English.

BACKGROUND OF THE INVENTION

Proteases are enzymes that cleave proteins at single, specific peptide bonds. Proteases can be classified into four generic classes: serine, thiol or cysteinyl, acid or aspartyl, and metalloproteases (Cuypers et al., J. Biol. Chem. 257:7086 (1982)). Proteases are essential to a variety of biological activities, such as digestion, formation and dissolution of blood clots, reproduction and the immune reaction to foreign cells and organisms. Aberrant proteolysis is associated with a number of disease states in man and other mammals. In many instances, it is beneficial to disrupt the function of one or more proteolytic enzymes in the course of therapeutically treating an animal.

The binding site for a peptide substrate consists of a series of "specificity subsites" across the surface of the enzyme. The term "specificity subsite" refers to a pocket or other site on the enzyme capable of interacting with a portion of a substrate for the enzyme. In discussing the interactions of peptides with proteases, e.g., serine and cysteine proteinases and the like, the present application utilizes the nomenclature of Schechter and Berger [(1967) Biochem. Biophys. Res. Commun. 27:157–162)]. The individual amino acid residues of a substrate or inhibitor are designated P1, P2, etc. and the corresponding subsites of the enzyme are designated S1, S2, etc, starting with the carboxy terminal residue produced in the cleavage reaction. The scissile bond of the substrate is amide bond between S1–S1' of the substrate. Thus, for the peptide Xaa1-Xaa2-Xaa3-Xaa4 which is cleaved between the Xaa3 and Xaa4 residues, the Xaa3 residue is referred to as the P1 residue and binds to the S1 subsite of the enzyme, Xaa2 is referred to as the P2 residue and binds to the S2 subsite, and so forth.

Dipeptidyl peptidase IV (DPIV), for example, is a serine protease which cleaves N-terminal dipeptides from a peptide chain containing, preferably, a proline residue in the penultimate position, e.g., in the P1 position. DPIV belongs to a group of cell-membrane-associated peptidases and, like the majority of cell-surface peptidases, is a type II integral membrane protein, being anchored to the plasma membrane by its signal sequence. DPIV is found in a variety of differentiated mammalian epithelia, endothelia and hemapoetic cells and tissues, including those of lymphoid origin where it is found specifically on the surface of CD4$^+$ T cells. DPIV has been identified as the leukocyte differentiation marker CD26.

SUMMARY OF THE INVENTION

One aspect of the invention provides a protease inhibitor represented by Formula I:

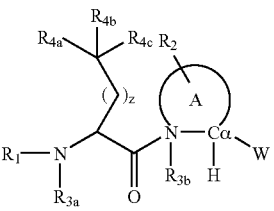

wherein

A represents a 3–8 membered heterocycle including the N and the Cα carbon;

W represents a functional group which reacts with an active site residue of the targeted protease to form a covalent adduct;

$R_1$ represents a hydrogen, a C-terminally linked amino acid or peptide or analog thereof, or amino protecting group;

$R_2$ is absent or represents one or more substitutions to the ring A, each of which can independently be a halogen, a lower alkyl, a lower alkenyl, a lower alkynyl, a carbonyl, a thiocarbonyl, an amino, an acylamino, an amido, a cyano, a nitro, an azido, a sulfate, a sulfonate, a sulfonamido, —(CH$_2$)$_m$—R$_6$, —(CH$_2$)$_m$—OH, —(CH$_2$)$_m$—O-lower alkyl, —(CH$_2$)$_m$—O-lower alkenyl, —(CH$_2$)$_n$—O—(CH$_2$)$_m$—R$_6$, —(CH$_2$)$_m$—SH, —(CH$_2$)$_m$—S-lower alkyl, —(CH$_2$)$_m$—S-lower alkenyl, —(CH$_2$)$_n$—S—(CH$_2$)$_m$—R$_6$;

$R_{3a}$ represents a hydrogen or a substituent which does not conjugate the electron pair of the nitrogen from which it pends;

$R_{3b}$ is absent, or represents a substituent which does not conjugate the electron pair of the nitrogen from which it pends, such as a lower alkyl;

$R_{4a}$ and $R_{4b}$ each independently represent a hydrogen, lower alkyl, heteroalkyl, cycloalkyl, heterocycloalkyl, aryl, heteroaryl, alkoxyl, carboxyl, carboxamide, carbonyl, or cyano, with the caveat that either both or neither of $R_{4a}$ and $R_{4b}$ are hydrogen;

$R_{4c}$ represents a halogen, an amine, an alkyl, heteroalkyl, cycloalkyl, heterocycloalkyl, aryl, heteroaryl, alkoxyl, carboxyl, carboxamide, carbonyl, or cyano;

$R_6$ represents, independently for each occurrence, an aryl, aralkyl, cycloalkyl, cycloalkenyl, or heterocycle moiety;

z is zero or an integer in the range of 1 to 3; m is zero or an integer in the range of 1 to 8; and n is an integer in the range of 1 to 8.

Another aspect of the invention provides a protease inhibitor represented by Formula III:

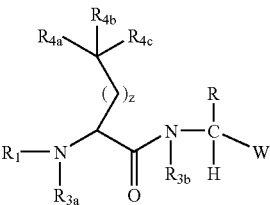

wherein

R represents hydrogen, a halogen, or a branched or unbranched C1–C6 alkyl;

W represents a functional group which reacts with an active site residue of the targeted protease to form a covalent adduct;

R$_1$ represents a hydrogen, a C-terminally linked amino acid or peptide or analog thereof, or amino protecting group;

R$_{3a}$ represents a hydrogen or a substituent which does not conjugate the electron pair of the nitrogen from which it pends, such as a lower alkyl;

R$_{3b}$ is absent, or represents a substituent which does not conjugate the electron pair of the nitrogen from which it pends, such as a lower alkyl;

R$_{4a}$ and R$_{4b}$ each independently represent a hydrogen, lower alkyl, heteroalkyl, cycloalkyl, heterocycloalkyl, aryl, heteroaryl, alkoxyl, carboxyl, carboxamide, carbonyl, or cyano, with the caveat that either both or neither of R$_{4a}$ and R$_{4b}$ are hydrogen;

R$_{4c}$ represents a halogen, an amine, an alkyl, heteroalkyl, cycloalkyl, heterocycloalkyl, aryl, heteroaryl, alkoxyl, carboxyl, carboxamide, carbonyl, or cyano; and z is zero or an integer in the range of 1 to 3.

Yet another aspect of the invention provides a protease inhibitor represented by Formula IV:

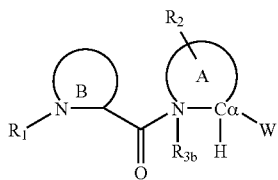

wherein

A represents a 3–8 membered heterocycle including the N and the Cα carbon;

B represents a C3–C8 ring, or C7–C14 fused bicyclic or tricyclic ring system;

W represents a functional group which reacts with an active site residue of the targeted protease to form a covalent adduct;

R$_1$ represents a hydrogen, a C-terminally linked amino acid or peptide or analog thereof, or amino protecting group;

R$_2$ is absent or represents one or more substitutions to the ring A, each of which can independently be a halogen, a lower alkyl, a lower alkenyl, a lower alkynyl, a carbonyl, a thiocarbonyl, an amino, an acylamino, an amido, a cyano, a nitro, an azido, a sulfate, a sulfonate, a sulfonamido, —(CH$_2$)$_m$—R$_6$, —(CH$_2$)$_m$—OH, —(CH$_2$)$_m$—O-lower alkyl, —(CH$_2$)$_m$—O-lower alkenyl, —(CH$_2$)$_n$—O—(CH$_2$)$_m$—R$_6$, —(CH$_2$)$_m$—SH, —(CH$_2$)$_m$—S-lower alkyl, —(CH$_2$)$_m$—S-lower alkenyl, —(CH$_2$)$_n$—S—(CH$_2$)$_m$—R$_6$;

R$_{3b}$ is absent, or represents a substituent which does not conjugate the electron pair of the nitrogen from which it pends, such as a lower alkyl;

R$_6$ represents, independently for each occurrence, an aryl, aralkyl, cycloalkyl, cycloalkenyl, or heterocycle moiety;

m is zero or an integer in the range of 1 to 8; and n is an integer in the range of 1 to 8.

Still another aspect of the invention relates to a protease inhibitor represented by Formula VI:

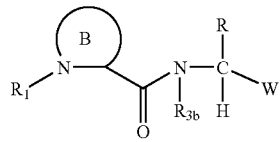

wherein

B represents a C3–C8 ring, or C7–C14 fused bicyclic or tricyclic ring system;

W represents a functional group which reacts with an active site residue of the targeted protease to form a covalent adduct;

R represents hydrogen, a halogen, or a branched or unbranched C1–C6 alkyl;

R$_1$ represents a hydrogen, a C-terminally linked amino acid or peptide or analog thereof, or amino protecting group; and R$_{3b}$ is absent, or represents a substituent which does not conjugate the electron pair of the nitrogen from which it pends, such as a lower alkyl.

In certain preferred embodiments, the W represents —CN, —CH=NR$_5$,

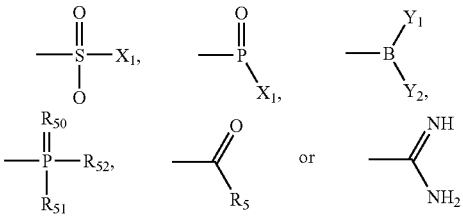

wherein,

Y$_1$ and Y$_2$ each independently represent —OH, or a group capable of being hydrolyzed to a hydroxyl group, including cyclic derivatives where Y$_1$ and Y$_2$ are connected via a ring having from 5 to 8 atoms in the ring structure;

R$_5$ represents H, an alkyl, an alkenyl, an alkynyl, —C(X$_1$)(X$_2$)X$_3$, —(CH$_2$)m-R$_6$, —(CH$_2$)n-OH, —(CH$_2$)n-O-alkyl, —(CH$_2$)n-O-alkenyl, —(CH$_2$)n-O-alkynyl, —(CH$_2$)n-O—(CH$_2$)m-R$_6$, —(CH$_2$)n-SH, —(CH$_2$)n-S-alkyl, —(CH$_2$)n-S-alkenyl, —(CH$_2$)n-S-alkynyl, —(CH$_2$)n-S—(CH$_2$)m-R$_6$, —C(O)C(O)NH$_2$, —C(O)C(O)OR$_7$;

R$_6$ represents, independently for each occurrence, an aryl, aralkyl, cycloalkyl, cycloalkenyl, or heterocycle moiety;

R$_7$ represents, independently for each occurrence, hydrogen, or an alkyl, alkenyl, aryl, aralkyl, cycloalkyl, cycloalkenyl, or heterocycle moiety;

R$_{50}$ represents O or S;

R$_{51}$ represents N$_3$, SH$_2$, NH$_2$, NO$_2$ or —OR$_7$;

R$_{52}$ represents hydrogen, a lower alkyl, an amine, —OR$_7$, or a pharmaceutically acceptable salt, or R$_{51}$ and R$_{52}$ taken together with the phosphorous atom to which they are attached complete a heterocyclic ring having from 5 to 8 atoms in the ring structure X$_1$ represents a halogen;

X$_2$ and X$_3$ each represent a hydrogen or a halogen;

m is zero or an integer in the range of 1 to 8; and n is an integer in the range of 1 to 8.

In certain preferred embodiments of the inhibitors, W represents:

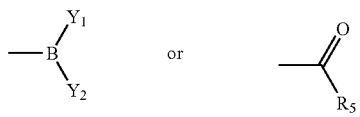

wherein, $Y_1$, $Y_2$, $R_5$ are as defined above.

In certain preferred embodiments, W represents —B(OH)$_2$, or a prodrug thereof which is hydrolyzed to —B(OH)$_2$ in vivo.

In certain other preferred embodiments, W represents —C(=O)—$R_5$, wherein $R_5$ is a hydrogen or —C($X_1$)($X_2$)$X_3$, wherein $X_1$ is a fluorine, and $X_2$ and $X_3$, if halogens, are also fluorine.

In certain embodiments of the inhibitors, $R_{4a}$, $R_{4b}$ and $R_{4c}$ each independently represent a small hydrophobic group, such as selected from the group consisting of halogens, lower alkyls, lower alkenyls, and lower alkynyls.

In certain embodiments of the inhibitors, $R_{4a}$ and $R_{4b}$ each represent hydrogen, and $R_{4c}$ represents a small hydrophobic group.

In certain embodiments of the inhibitors, $R_{4a}$ and $R_{4b}$ each represent hydrogen, and $R_{4c}$ represents a cycloalkyl, heterocycloalkyl, aryl, or heteroaryl, and in certain preferred embodiments, is a C3–C8 cycloalkyl.

In certain embodiments of the inhibitors, $R_2$ is absent, or represents —OH.

In certain embodiments of the inhibitors, $R_{3a}$ a hydrogen and $R_{3b}$ is absent.

In certain embodiments of the inhibitors, $R_1$ is an amino acid residue or a peptidyl moiety which is a substrate for a protease.

In certain embodiments of the inhibitors, the protease inhibitor inhibits DPIV with a Ki of 50 nm or less.

In certain embodiments of the inhibitors, the inhibitor is orally active.

In certain embodiments of the inhibitors, the inhibitor has a therapeudic index in humans of at least 2, and even more preferably 5, 10 or even 100, e.g., such as a therapeudic index for regulating glucose metabolism.

Another aspect of the invention provides a pharmaceutical composition comprising a pharmaceutically acceptable carrier and one or more of the subject protease inhibitors, or a pharmaceutically acceptable salt or prodrug thereof.

Another aspect of the invention provides for use of one or more of the subject inhibitors in the manufacture of a medicament for inhibiting a post-proline cleaving enzyme in vivo. For example, the subject inhibitors can be used to manufacture medicaments for increasing plasma concentrations of one or peptide hormones processed by post-proline cleaving enzymes (e.g., DP-IV and the like). Exemplary medicaments are useful in increasing plasma concentrations of such hormones as glucagons-like peptide, NPY, PPY, secretin, GLP-1, GLP-2, and GIP.

In certain preferred embodiments, the subject inhibitors can be used to manufacture medicaments for regulating glucose metabolism, such as for use in treating patients suffering from Type II diabetes, insulin resistance, glucose intolerance, hyperglycemia, hypoglycemia, hyperinsulinemia, obesity, hyperlipidemia, or hyperlipoproteinemia.

Yet another aspect of the invention provides a packaged pharmaceutical comprising: a preparation of one or more of the subject protease inhibitor; a pharmaceutically acceptable carrier; and instructions, written and/or pictorial, describing the use of the preparation for inhibiting a post-proline cleaving enzyme in vivo, such as for regulating glucose metabolism.

The packaged pharmaceutical can also include, e.g., as co-formulation the protease inhibitor or simply co-packaged, insulin and/or an insulinotropic agent.

The packaged pharmaceutical can also include, e.g., as co-formulation the protease inhibitor or simply co-packaged, an M1 receptor antagonist, a prolactin inhibitor, agents acting on the ATP-dependent potassium channel of β-cells, metformin, and/or glucosidase inhibitors.

The present invention also relates to improved methods for the long-term reduction and abatement of at least one of the foregoing disorders based on a therapeutic regimen administered over the short-term.

The present invention further provides a method for regulating, and altering on a long-term basis, the glucose and lipogenic responses of vertebrate animals, including humans.

In particular, the compounds of the invention may be employed to provide methods for producing long lasting beneficial changes in one or more of the following: the sensitivity of the cellular response of a species to insulin (reduction of insulin resistance), blood insulin levels, hyperinsulinemia, blood glucose levels, the amount of body fat stores, blood lipoprotein levels, and thus to provide effective treatments for diabetes, obesity and/or atherosclerosis.

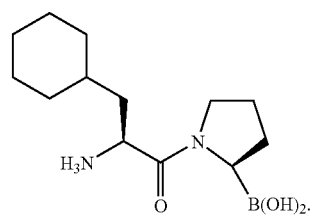

Figure 11:
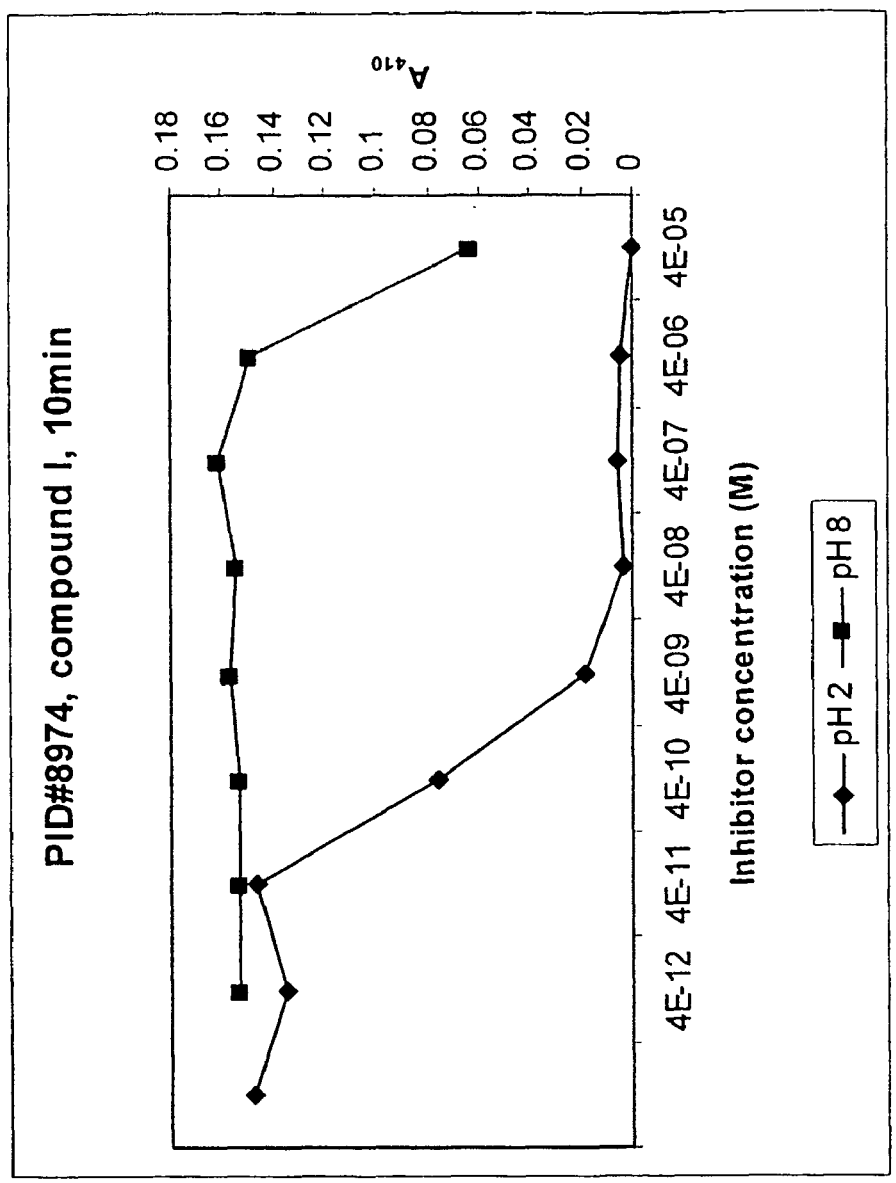
Figure 11:
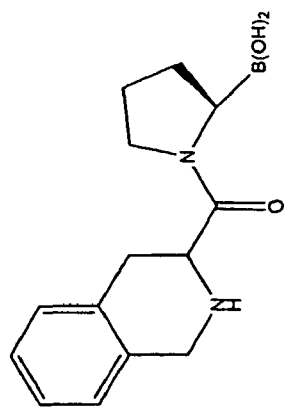

FIG. 11 is a graph showing the DPIV inhibitory activity of 1,2,3,4-tetrahydroisoquinoline-boroProline,

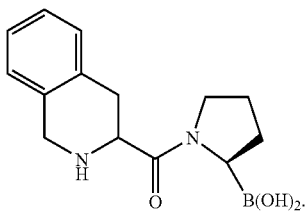

Figure 12:
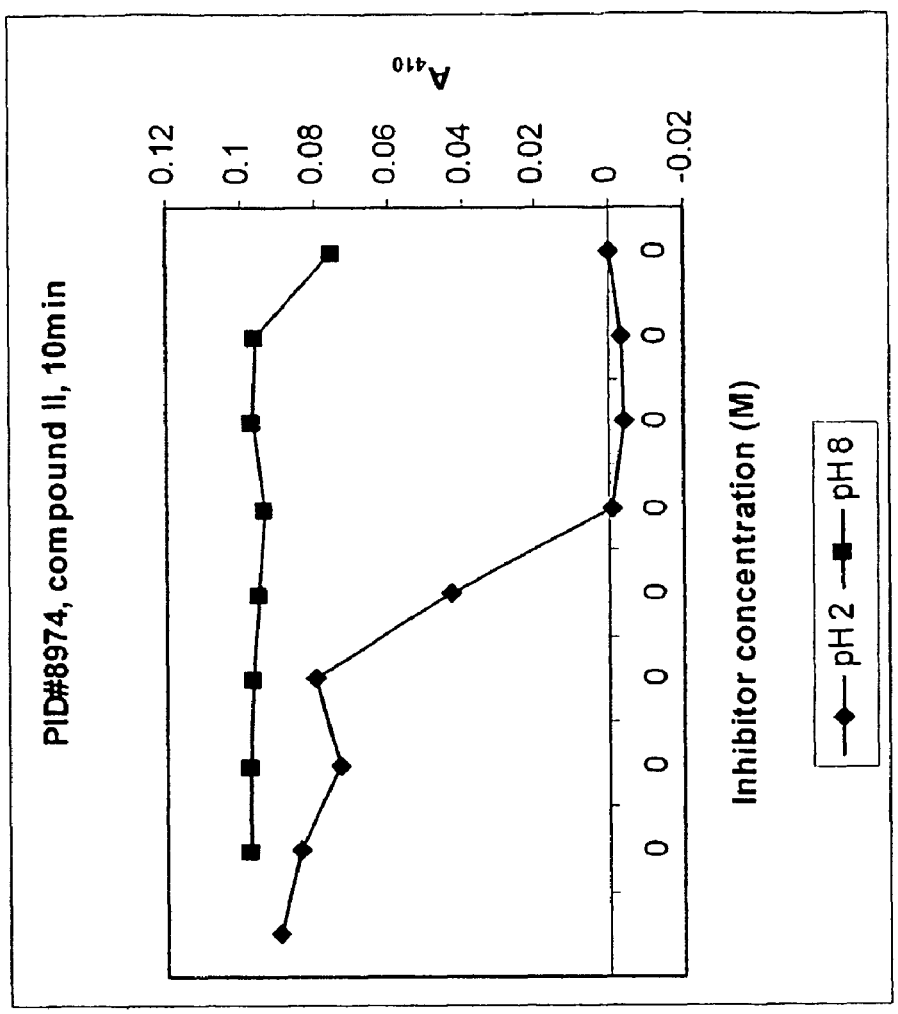
Figure 12:
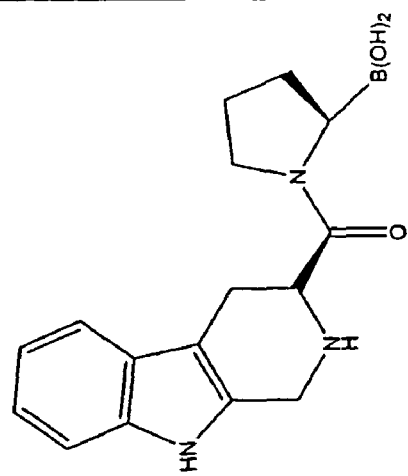

FIG. 12 is a graph showing the DPIV inhibitory activity of 1,2,3,4-tetrahydro-beta-carboline-boroProline,

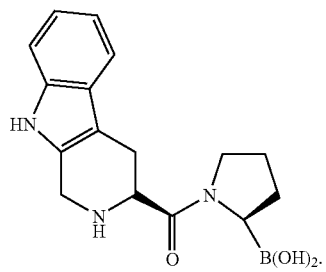

Figure 13:
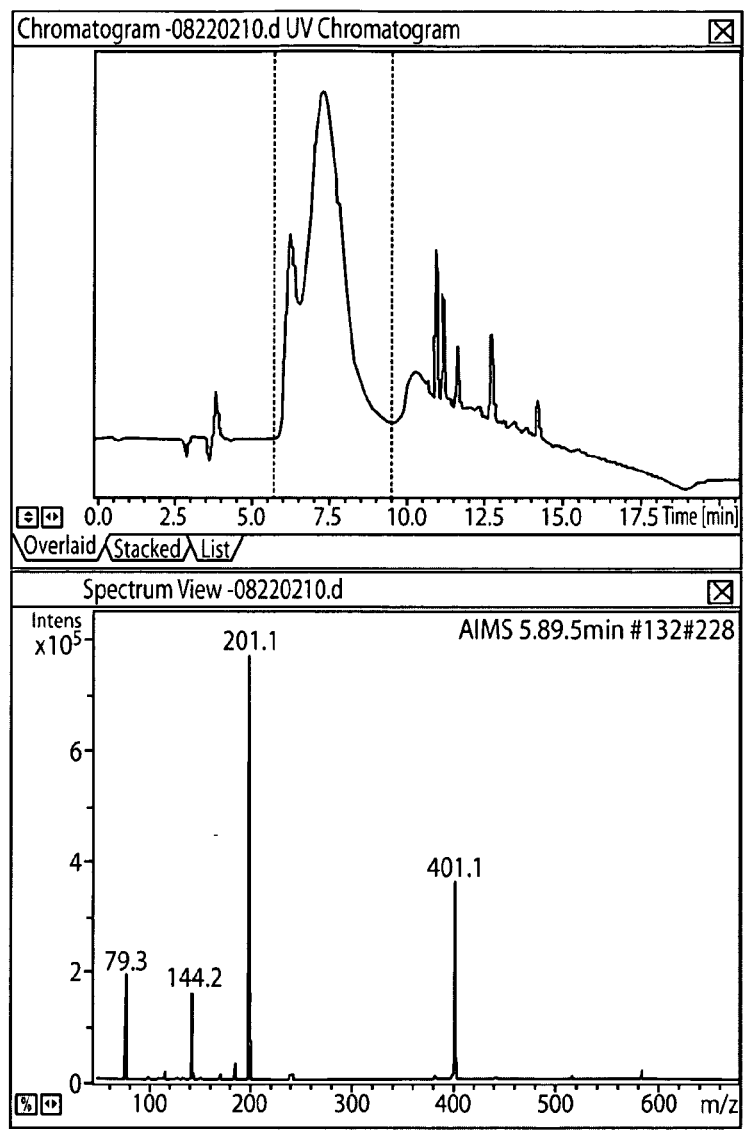
Figure 13:
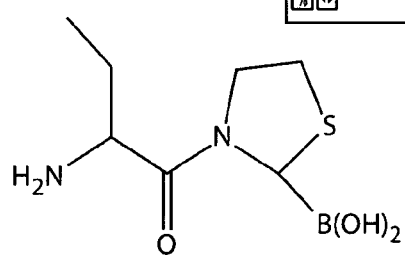

FIG. 13 are two graphs, MS and NMR, showing the purification of Ethylglycine-2-boroThiazolidine,

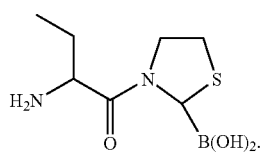

Figure 14:
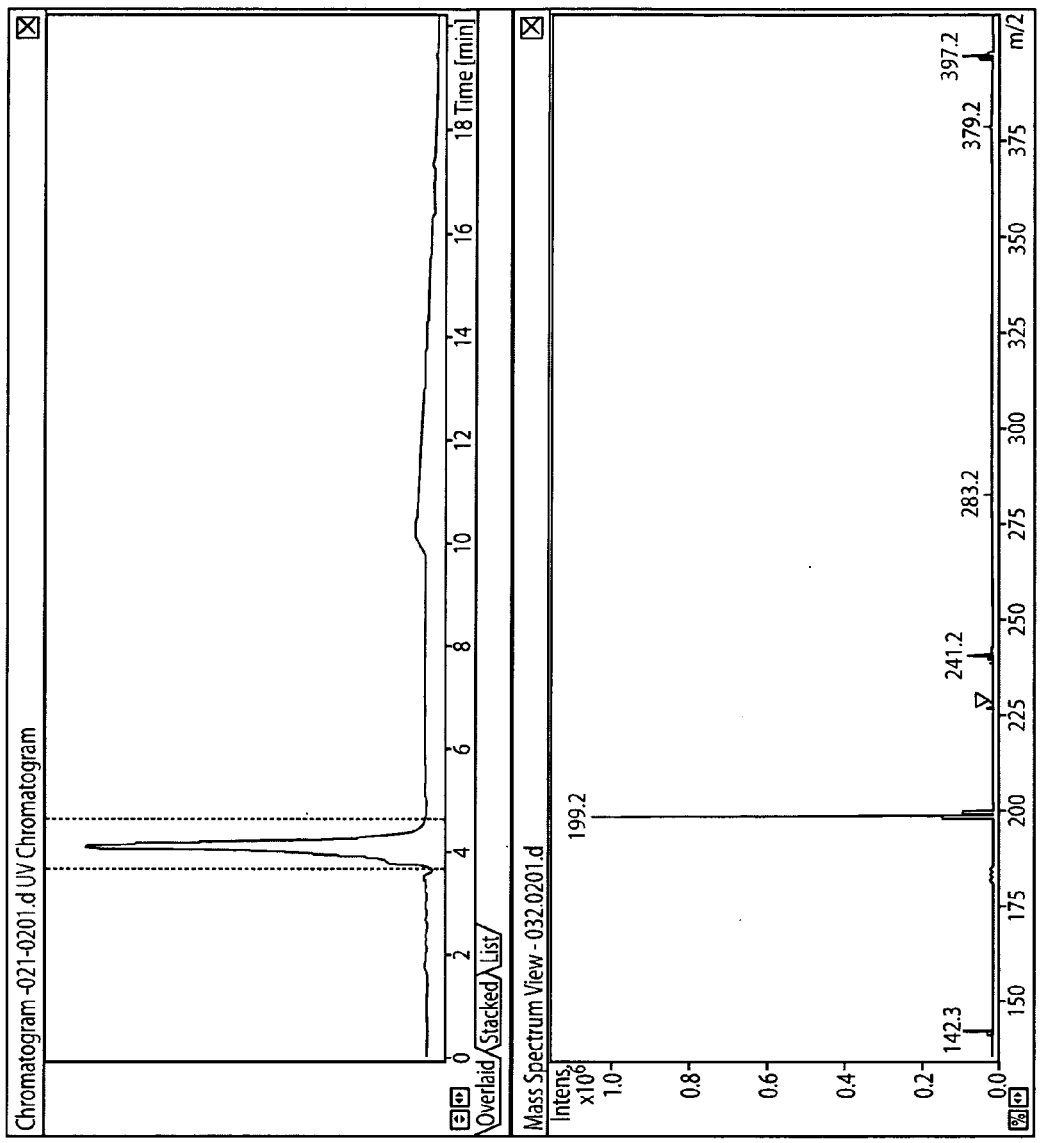

FIG. 14 are two graphs, UV and MS, showing the purification of Ethylglycine-boroHydroxyproline,

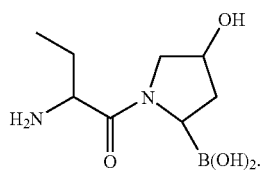

Figure 15:
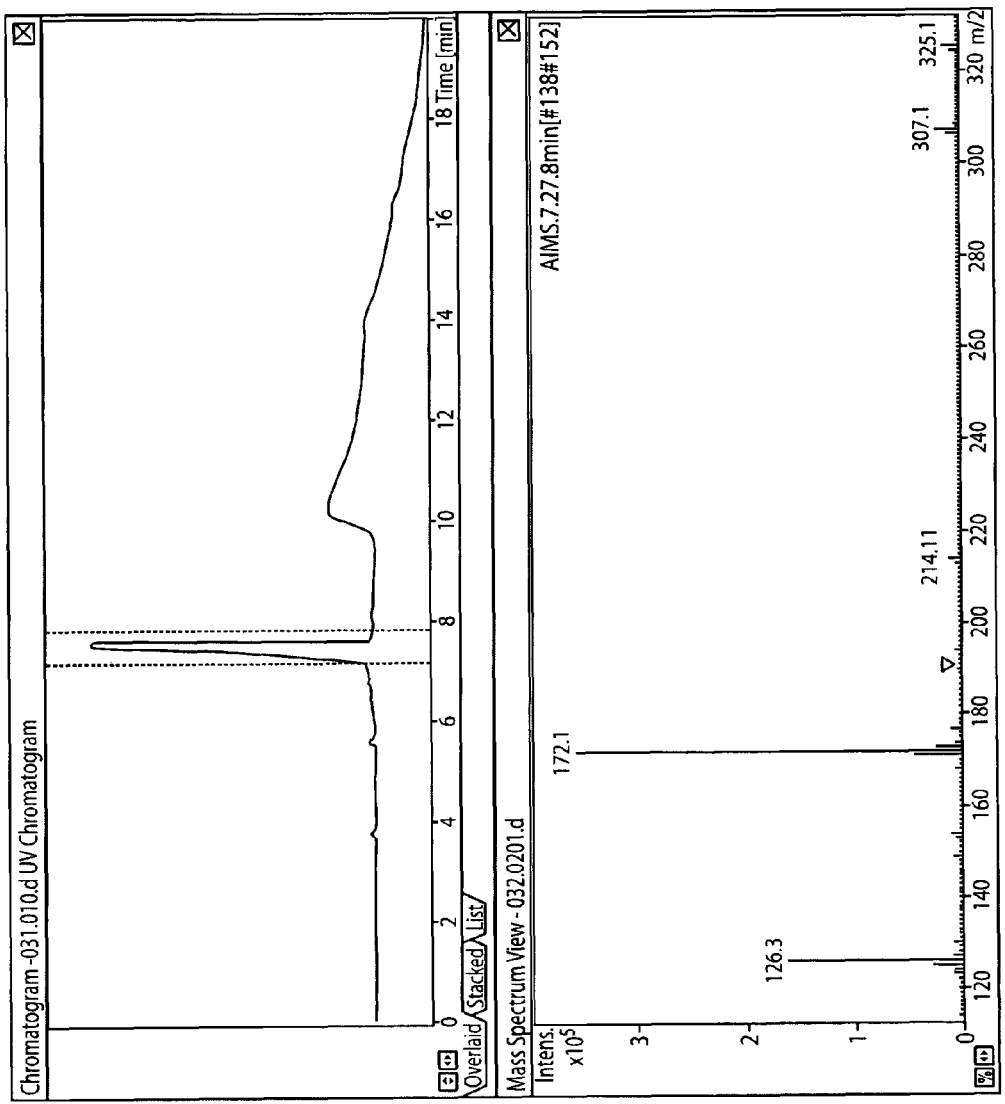

FIG. 15 are two graphs, UV and MS, showing the purification of diaminoglycine-boroProline,

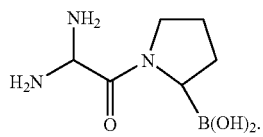

Figure 16:
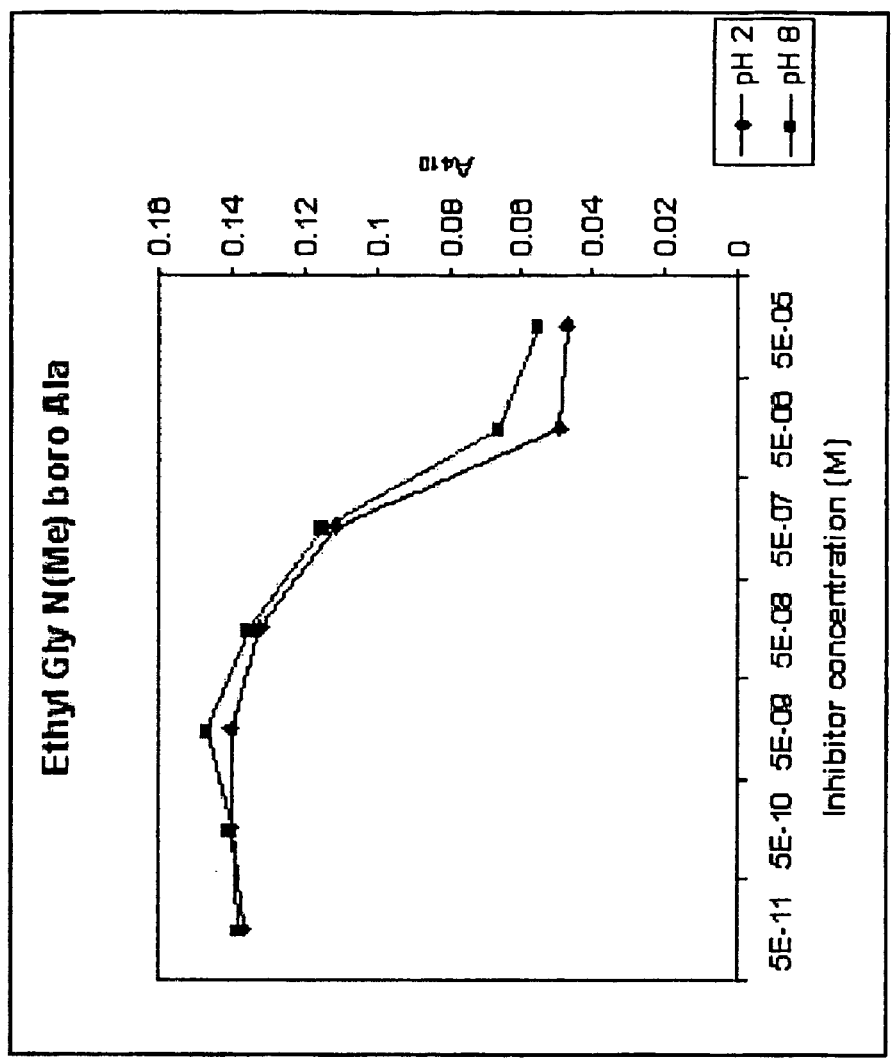
Figure 16:
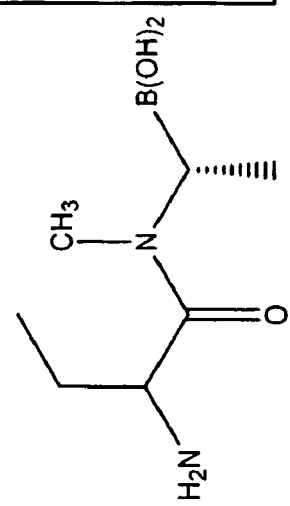

FIG. 16 is a graph showing the DPIV inhibitory activity of Ethylglycine-N(methyl)boroAlanine,

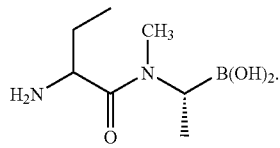

Figure 17:
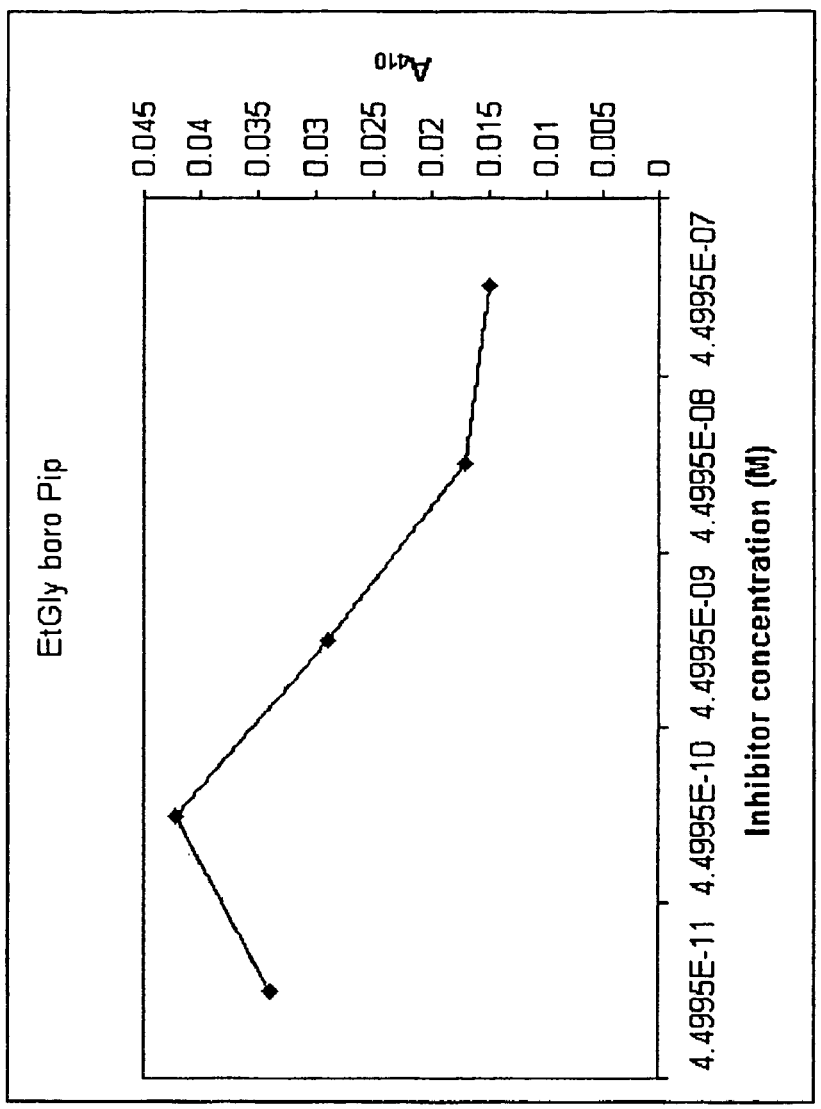
Figure 17:
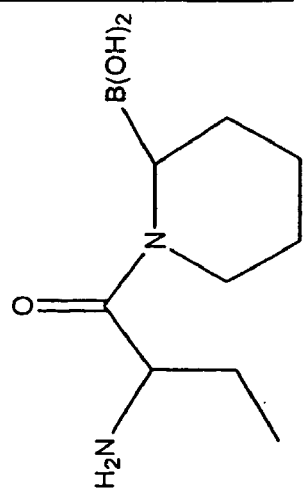

FIG. 17 is a graph showing the DPIV inhibitory activity of Ethylglycine-boroPiperidine,

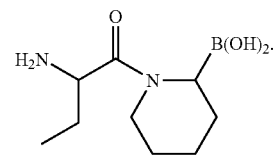

Figure 18:
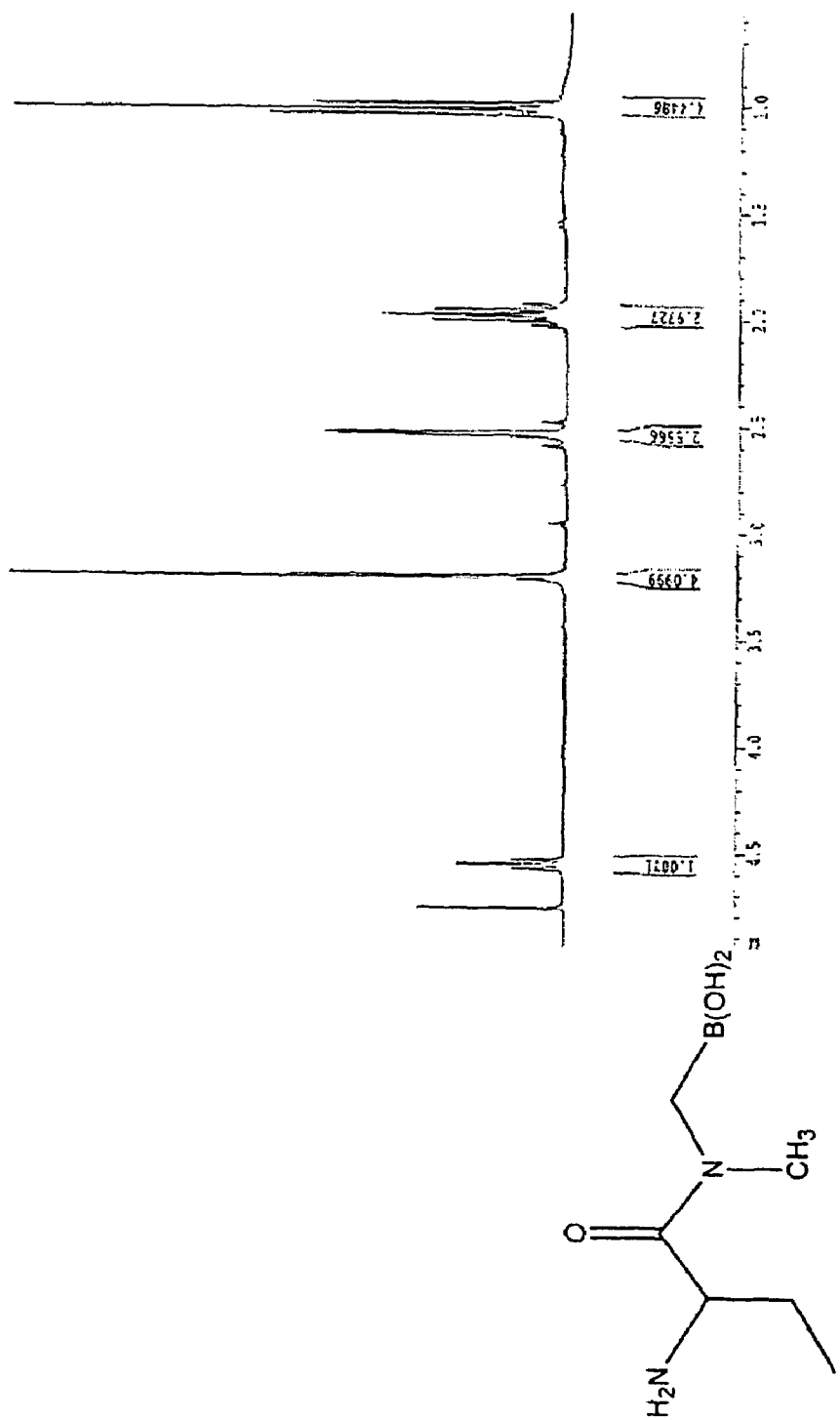

FIG. 18 is an NMR spectra for Ethylglycine-N(methyl)boroGlycine,

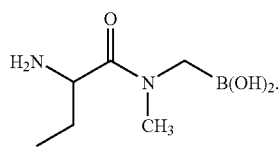

Figure 19:
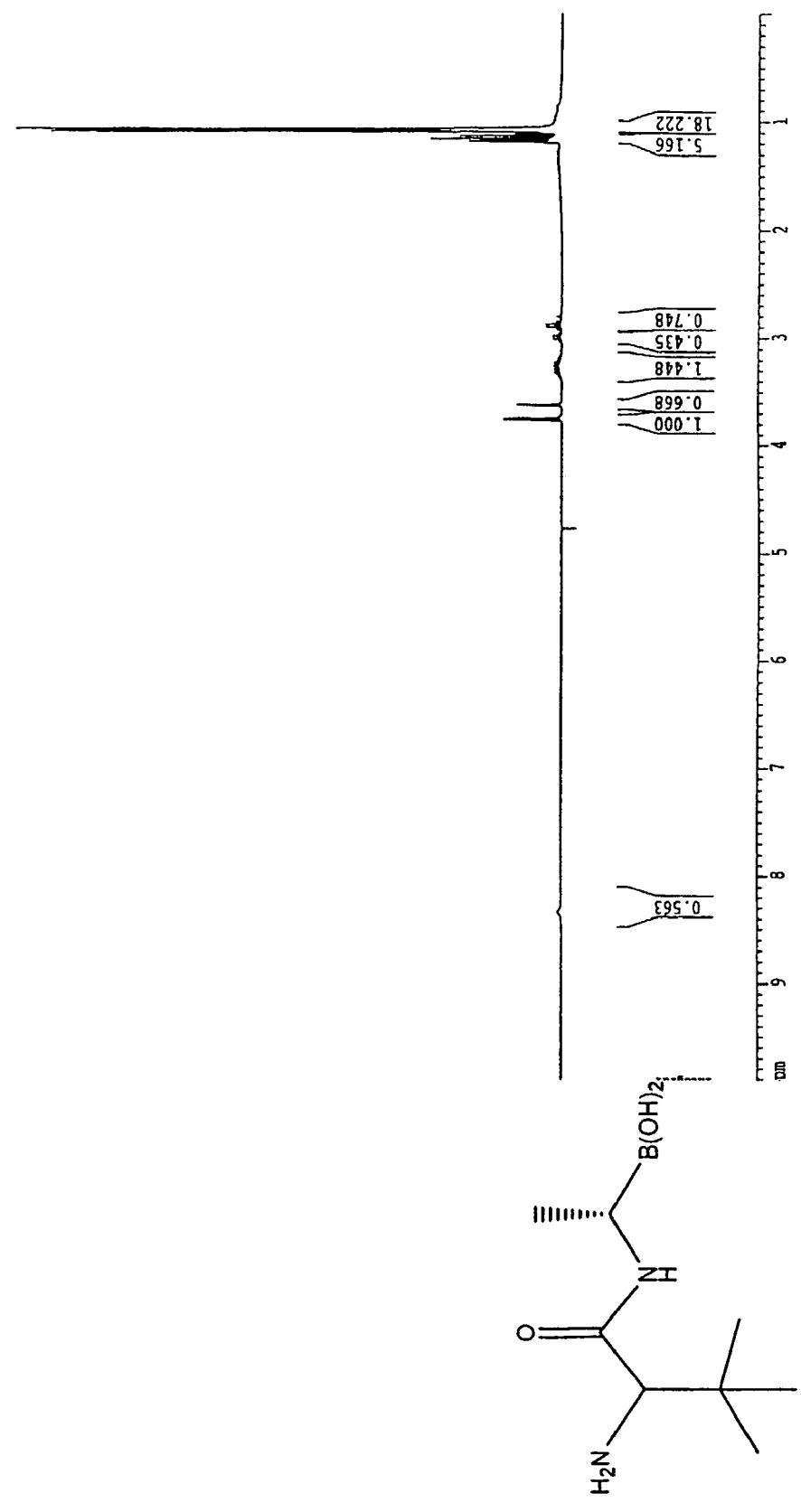

FIG. 19 is an NMR spectra for t-butylglycine-boroAlanine,

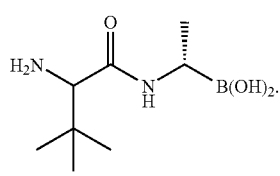

Figure 20:
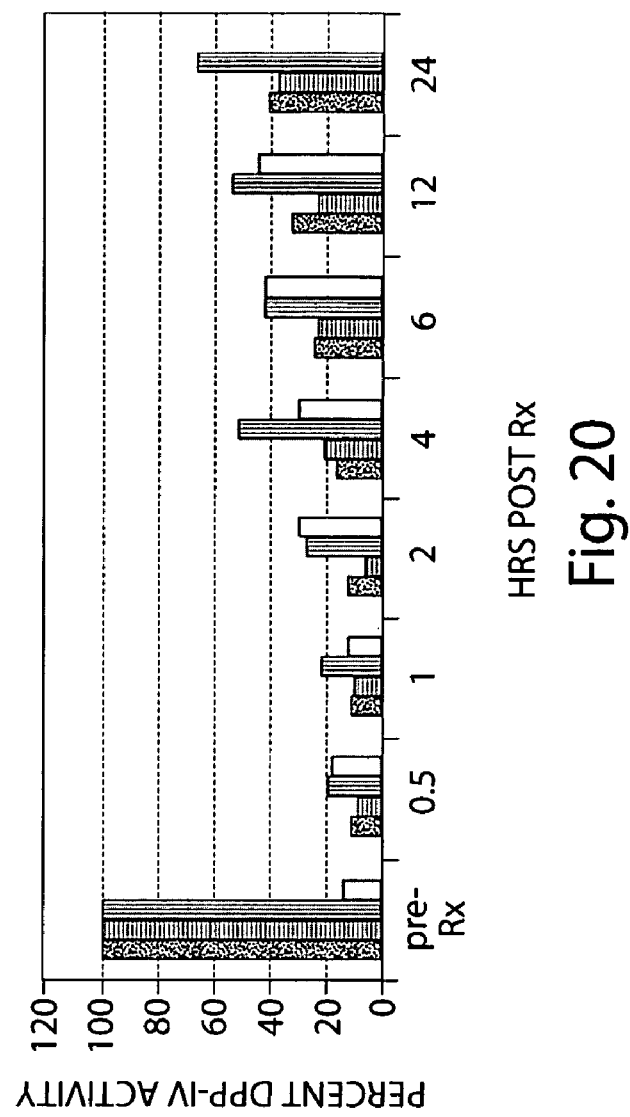
Figure 20:
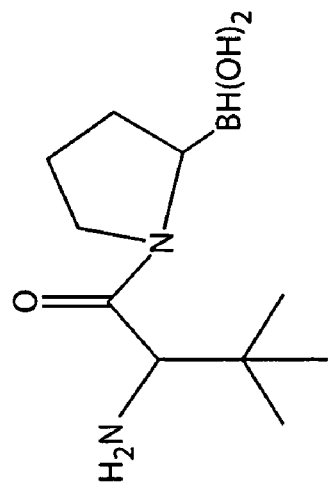

FIG. 20 is a graph showing the in vivo DPIV inhibitory activity, at 0.05 mg/kg, of t-butylglycine-boroProline,

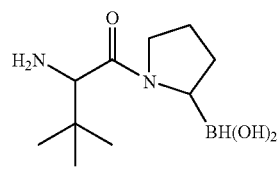

Figure 21:
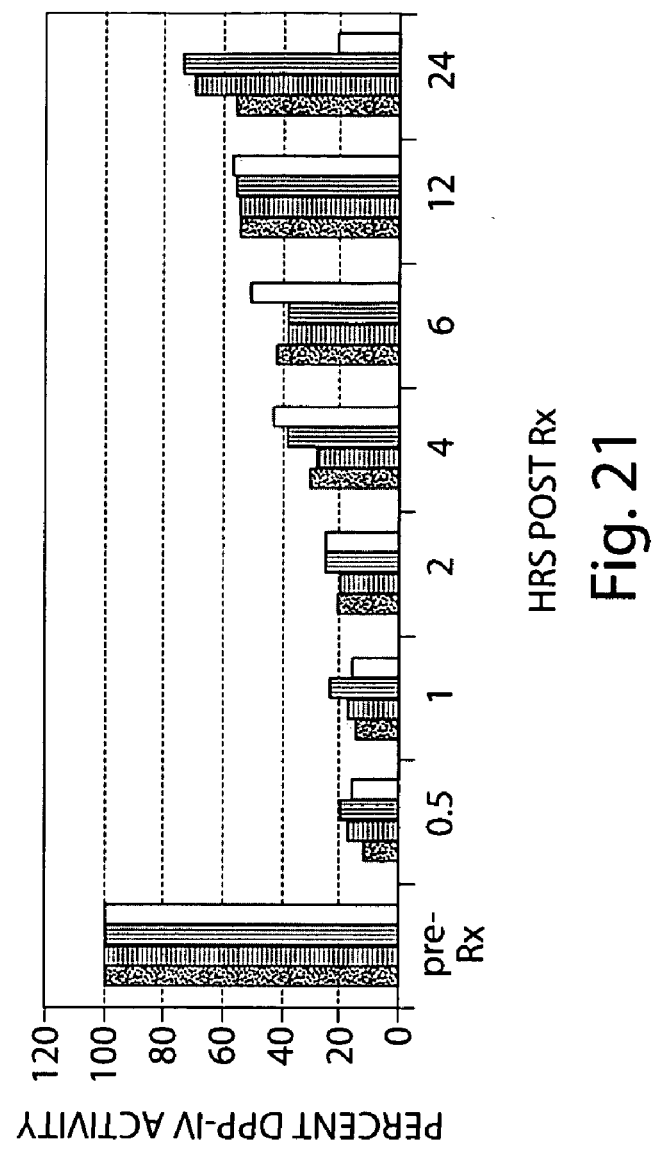
Figure 21:
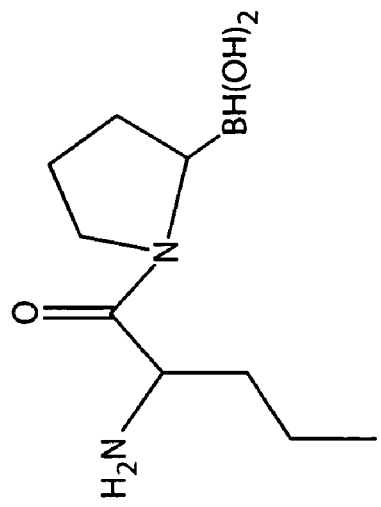

FIG. 21 is a graph showing the in vivo DPIV inhibitory activity, at 0.05 mg/kg, of isopropylglycine-boroProline,

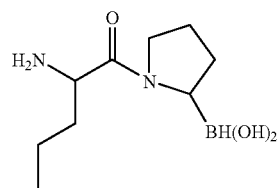

Figure 22:
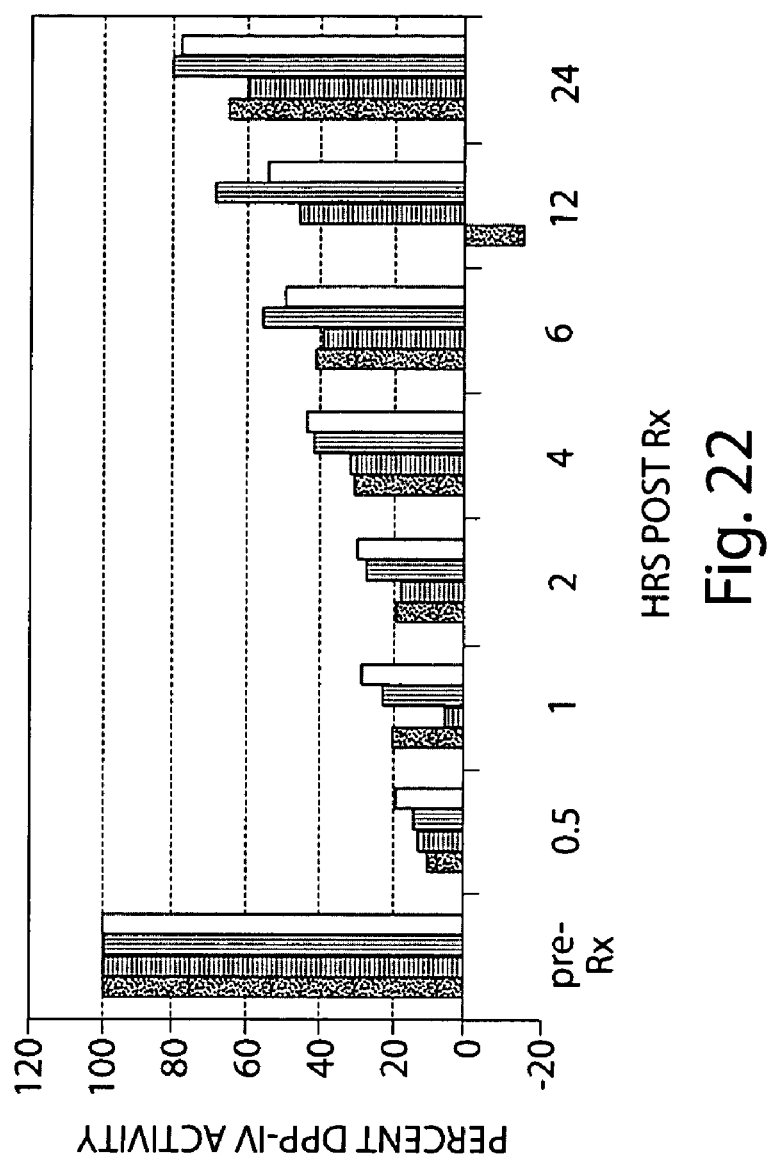
Figure 22:
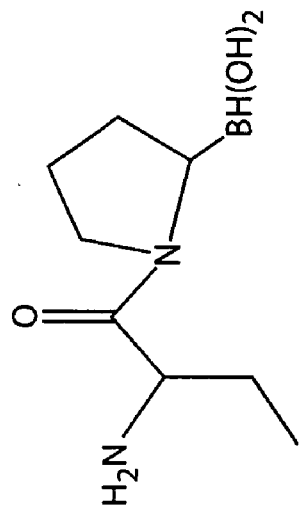

FIG. 22 is a graph showing the in vivo DPIV inhibitory activity, at 0.05 mg/kg, of ethylglycine-boroProline,

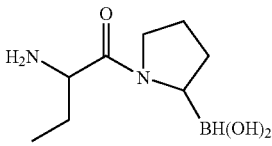

Figure 23:
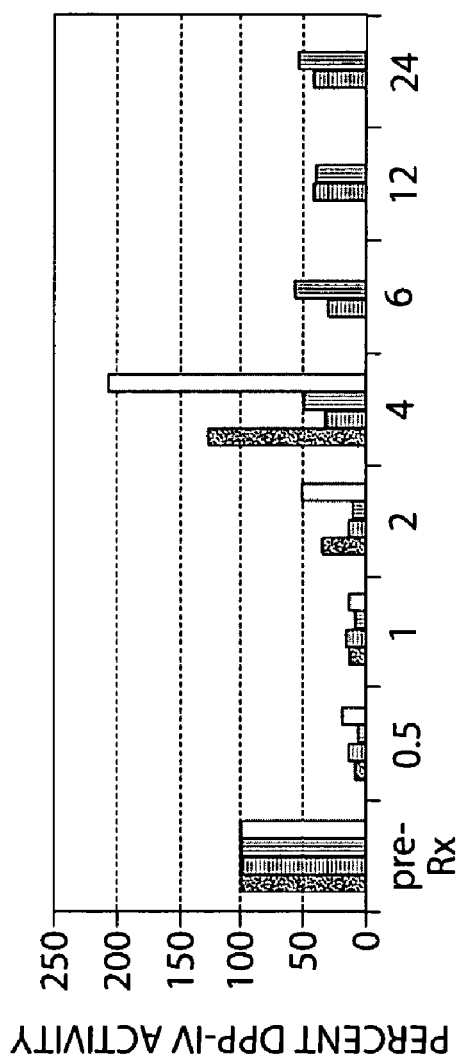
Figure 23:
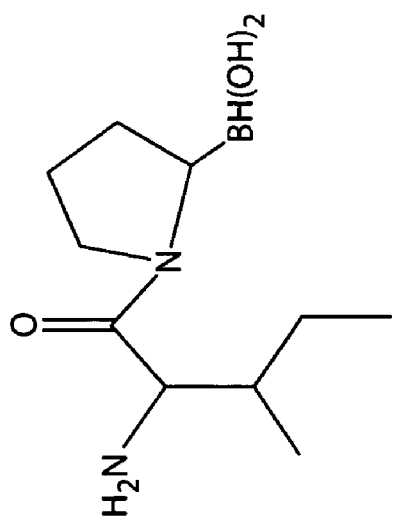

FIG. 23 is a graph showing the in vivo DPIV inhibitory activity, at 0.05 mg/kg, of (allo)isoleucine-boroProline,

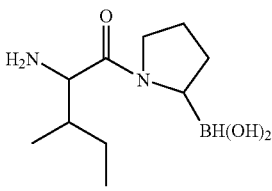

DETAILED DESCRIPTION

I. Overview

The present invention relates to inhibitors of post-proline cleaving enzymes, such as inhibitors of dipeptidyl peptidase IV, as well as pharmaceutical compositions thereof, and methods for using such inhibitors. In particular, the inhibitors of the present invention are improved over those in the prior art by selection of particular classes of sidechains in the P1 and/or P2 position of the inhibitor. Salient features for compounds of the present invention include: better therapeutic indices, owing in part to reduced toxicity and/or improved specificity for the targeted protease; better oral availability; increased shelf-life; and/or increased duration of action (such as single oral dosage formulations which are effective for more than 4 hours, and even more preferably for more 8, 12 or 16 hours).

The compounds of the present invention can be used as part of treatments for a variety of disorders/conditions, such as those which are mediated by DPIV. For instance, the subject inhibitors can be used to up-regulate GIP and GLP-1 activities, e.g., by increasing the half-life of those hormones, as part of a treatment for regulating glucose levels and/or metabolism, e.g., to reduce insulin resistance, treat hyperglycemia, hyperinsulinemia, obesity, hyperlipidemia, hyperlipoprotein-emia (such as chylomicrons, VLDL and LDL), and to regulate body fat and more generally lipid stores, and, more generally, for the improvement of metabolism disorders, especially those associated with diabetes, obesity and/or atherosclerosis.

While not wishing to bound by any particular theory, it is observed that compounds which inhibit DPIV are, correlatively, able to improve glucose tolerance (See Examples 2 and 4), though not necessarily through mechanisms involving DPIV inhibition per se. Indeed, the applicant has previously demonstrated an effect in mice lacking a GLP-1 receptor suggesting that the subject method may not include a mechanism of action directly implicating GLP-1 itself, though it has not been ruled out that GLP-1 may have other receptors. However, in light of the correlation with DPIV inhibition, in preferred embodiments, the subject method utilizes an agent with a Ki for DPIV inhibition of 50.0 nm or less, more preferably of 10.0 nm or less, and even more preferably of 1.0, 0.1 or even 0.01 nM or less. Indeed, inhibitors with Ki values in the picomolar and even femtomolar range are contemplated. Thus, while the active agents are described herein, for convenience, as "DPIV inhibitors", it will be understood that such nomenclature is not intending to limit the subject invention to a particular mechanism of action.

Certain of the subject compounds have extended duration. Accordingly, in certain preferred embodiments, the inhibitor(s) is selected, and the amount of inhibitor formulated, to provide a dosage which inhibits serum PPCE (e.g., DPIV) levels by at least 50 percent for at least 4 hours after a single dose, and even more preferably for at least 8 hours or even 12 or 16 hours after a single dose.

For instance, in certain embodiments the method involves administration of a DPIV inhibitor, preferably at a predetermined time(s) during a 24-hour period, in an amount effective to improve one or more aberrant indices associated with glucose metabolism disorders (e.g., glucose intolerance, insulin resistance, hyperglycemia, hyperinsulinemia and Type I and II diabetes).

In other embodiments, the method involves administration of a DPIV inhibitor in an amount effective to improve aberrant indices associated with obesity. Fat cells release the hormone leptin, which travels in the bloodstream to the brain and, through leptin receptors there, stimulates production of GLP-1. GLP-1, in turn, produces the sensation of being full. The leading theory is that the fat cells of most obese people probably produce enough leptin, but leptin may not be able to properly engage the leptin receptors in the brain, and so does not stimulate production of GLP-1. There is accordingly a great deal of research towards utilizing preparations of GLP-1 as an appetite suppressant. The subject method provides a means for increasing the half-life of both endogenous and ectopically added GLP-1 in the treatment of disorders associated with obesity.

In a more general sense, the present invention provides methods and compositions for altering the pharmokinetics of a variety of different polypeptide hormones by inhibiting the proteolysis of one or more peptide hormones by DPIV or some other proteolytic activity. Post-secretory metabolism is an important element in the overall homeostasis of regulatory peptides, and the other enzymes involved in these processes may be suitable targets for pharmacological intervention by the subject method.

For example, the subject method can be used to increase the half-life of other proglucagon-derived peptides, such as glicentin (corresponding to PG 1–69), oxyntomodulin (PG 33–69), glicentin-related pancreatic polypeptide (GRPP, PG 1–30), intervening peptide-2 (IP-2, PG 111–122amide), and glucagon-like peptide-2 (GLP-2, PG 126–158).

GLP-2, for example, has been identified as a factor responsible for inducing proliferation of intestinal epithelium. See, for example, Drucker et al. (1996) PNAS 93:7911. The subject method can be used as part of a regimen for treating injury, inflammation or resection of intestinal tissue, e.g., where enhanced growth and repair of the intestinal mucosal epithelial is desired, such as in the treatment of Chron's disease or Inflammatory Bowel Disease (IBD).

DPIV has also been implicated in the metabolism and inactivation of growth hormone-releasing factor (GHRF). GHRF is a member of the family of homologous peptides that includes glucagon, secretin, vasoactive intestinal peptide (VIP), peptide histidine isoleucine (PHI), pituitary adenylate cyclase activating peptide (PACAP), gastric inhibitory peptide (GIP) and helodermin. Kubiak et al. (1994) Peptide Res 7:153. GHRF is secreted by the hypothalamus, and stimulates the release of growth hormone (GH) from the anterior pituitary. Thus, the subject method can be used to improve clinical therapy for certain growth hormone deficient children, and in clinical therapy of adults to improve nutrition and to alter body composition (muscle vs. fat). The subject method can also be used in veterinary practice, for example, to develop higher yield milk production and higher yield, leaner livestock.

Likewise, the DPIV inhibitors of the subject invention can be used to alter the plasma half-life of secretin, VIP, PHI, PACAP, GIP and/or helodermin. Additionally, the subject method can be used to alter the pharmacokinetics of Peptide YY and neuropeptide Y, both members of the pancreatic polypeptide family, as DPIV has been implicated in the processing of those peptides in a manner which alters receptor selectivity.

In other embodiments, the subject inhibitors can be used to stimulate hematopoiesis.

In still other embodiments, the subject inhibitors can be used to inhibit growth or vascularization of transformed cells/tissues, e.g., to inhibit cell proliferation such as that associated with tumor growth and metastasis, and for inhibiting angiogenesis in an abnormal proliferative cell mass.

In yet other embodiments, the subject inhibitors can be used to reduce immunological responses, e.g., as an immunosuppressant.

In yet other examples, the DPIV inhibitors according to the present invention can be used to treat CNS maladies such as strokes, tumors, ischemia, Parkinson's disease, memory loss, hearing loss, vision loss, migraines, brain injury, spinal cord injury, Alzheimer's disease and amyotrophic lateral sclerosis (which has a CNS component). Additionally, the DPIV inhibitors can be used to treat disorders having a more peripheral nature, including multiplesclerosis and diabetic neuropathy.

Another aspect of the present invention relates to pharmaceutical compositions of the subject post-proline cleaving enzyme inhibitors, particularly DPIV inhibitors, and their uses in treating and/or preventing disorders which can be improved by altering the homeostasis of peptide hormones. In a preferred embodiment, the inhibitors have hypoglycemic and antidiabetic activities, and can be used in the treatment of disorders marked by aberrant glucose metabolism (including storage). In particular embodiments, the compositions of the subject methods are useful as insulinotropic agents, or to potentiate the insulinotropic effects of such molecules as GLP-1. In this regard, certain embodiments of the present compositions can be useful for the treatment and/or prophylaxis of a variety of disorders, including one or more of: hyperlipidemia, hyperglycemia, obesity, glucose tolerance insufficiency, insulin resistance and diabetic complications.

In general, the inhibitors of the subject method will be small molecules, e.g., with molecular weights less than 7500 amu, preferably less than 5000 amu, and even more preferably less than 2000 or even 1000 amu. In preferred embodiments, the inhibitors will be orally active.

II. Definitions

The term "high affinity" as used herein means strong binding affinity between molecules with a dissociation constant $K_D$ of no greater than 1 μM. In a preferred case, the $K_D$ is less than 100 nM, 10 nM, 1 nM, 100 pM, or even 10 pM or less. In a most preferred embodiment, the two molecules can be covalently linked ($K_D$ is essentially 0).

The term "boro-Ala" refers to the analog of alanine in which the carboxylate group (COOH) is replaced with a boronyl group (B(OH)$_2$). Likewise, the term "boro-Pro" refers to the analog of praline in which the carboxylate group (COOH) is replaced with a boronyl group (B(OH)$_2$). More generally, the term "boro-Xaa", where Xaa is an amino acid residue, refers to the analog of an amino acid in which the carboxylate group (COOH) is replaced with a boronyl group (B(OH)$_2$).

A "patient" or "subject" to be treated by the subject method can mean either a human or non-human subject.

The term "$ED_{50}$" means the dose of a drug that, in 50% of patients, will provide a clinically relevant improvement or change in a physiological measurement, such as glucose responsiveness, increase in hematocrit, decrease in tumor volume, etc.

The term "$IC_{50}$" means the dose of a drug that inhibits a biological activity by 50%, e.g., the amount of inhibitor required to inhibit at least 50% of DPIV (or other PPCE) activity in vivo.

A compound is said to have an "insulinotropic activity" if it is able to stimulate, or cause the stimulation of, the synthesis or expression of the hormone insulin.

The term "interact" as used herein is meant to include all interactions (e.g., biochemical, chemical, or biophysical interactions) between molecules, such as protein-protein, protein-nucleic acid, nucleic acid-nucleic acid, protein-small molecule, nucleic acid-small molecule or small molecule-small molecule interactions.

The term "$LD_{50}$" means the dose of a drug that is lethal in 50% of test subjects.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic, (i.e., it is intended to diminish, ameliorate, or stabilize the existing unwanted condition or side effects thereof).

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "therapeutic index" refers to the therapeutic index of a drug defined as $LD_{50}/ED_{50}$.

A "therapeutically effective amount" of a compound, e.g., such as a DPIV inhibitor of the present invention, with respect to the subject method of treatment, refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

A "single oral dosage formulation" is a dosage which provides an amount of drug to produce a serum concentration at least as great as the $EC_{50}$ for that drug, but less than the $LD_{50}$. Another measure for a single oral dosage formulation is that it provides an amount of drug necessary to produce a serum concentration at least as great as the $IC_{50}$ for that drug, but less than the $LD_{50}$. By either measure, a single oral dosage formulation is preferably an amount of drug which produces a serum concentration at least 10 percent less than the $LD_{50}$, and even more preferably at least 50 percent, 75 percent or even 90 percent less than the drug's the $LD_{50}$.

An aliphatic chain comprises the classes of alkyl, alkenyl and alkynyl defined below. A straight aliphatic chain is limited to unbranched carbon chain radicals. As used herein, the term "aliphatic group" refers to a straight chain, branched-chain, or cyclic aliphatic hydrocarbon group and includes saturated and unsaturated aliphatic groups, such as an alkyl group, an alkenyl group, and an alkynyl group.

Alkyl refers to a fully saturated branched or unbranched carbon chain radical having the number of carbon atoms specified, or up to 30 carbon atoms if no specification is made. For example, alkyl of 1 to 8 carbon atoms refers to radicals such as methyl, ethyl, propyl, butyl, pentyl, hexyl, heptyl, and octyl, and those radicals which are positional isomers of these radicals. Alkyl of 10 to 30 carbon atoms includes decyl, undecyl, dodecyl, tridecyl, tetradecyl, pentadecyl, hexadecyl, heptadecyl, octadecyl, nonadecyl, eicosyl, heneicosyl, docosyl, tricosyl and tetracosyl. In preferred embodiments, a straight chain or branched chain alkyl has 30 or fewer carbon atoms in its backbone (e.g., $C_1$–$C_{30}$ for straight chains, $C_3$–$C_{30}$ for branched chains), and more preferably 20 or fewer. Likewise, preferred cycloalkyls have from 3–10 carbon atoms in their ring structure, and more preferably have 5, 6 or 7 carbons in the ring structure.

Unless the number of carbons is otherwise specified, "lower alkyl", as used herein, means an alkyl group, as defined above, but having from one to ten carbons, more preferably from one to six carbon atoms in its backbone structure such as methyl, ethyl, n-propyl, isopropyl, n-butyl, isobutyl, sec-butyl, and tert-butyl. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

The term "alkylthio" refers to an alkyl group, as defined above, having a sulfur radical attached thereto. In preferred embodiments, the "alkylthio" moiety is represented by one of —(S)-alkyl, —(S)-alkenyl, —(S)-alkynyl, and —(S)—$(CH_2)_m$—$R_1$, wherein m and $R_1$ are defined below. Representative alkylthio groups include methylthio, ethylthio, and the like.

Alkenyl refers to any branched or unbranched unsaturated carbon chain radical having the number of carbon atoms specified, or up to 26 carbon atoms if no limitation on the number of carbon atoms is specified; and having 1 or more double bonds in the radical. Alkenyl of 6 to 26 carbon atoms is exemplified by hexenyl, heptenyl, octenyl, nonenyl, decenyl, undecenyl, dodenyl, tridecenyl, tetradecenyl, pentadecenyl, hexadecenyl, heptadecenyl, octadecenyl, nonadecenyl, eicosenyl, heneicosoenyl, docosenyl, tricosenyl and tetra-cosenyl, in their various isomeric forms, where the unsaturated bond(s) can be located anywhere in the radical and can have either the (Z) or the (E) configuration about the double bond(s).

Alkynyl refers to hydrocarbyl radicals of the scope of alkenyl, but having 1 or more triple bonds in the radical.

The terms "alkoxyl" or "alkoxy" as used herein refers to an alkyl group, as defined below, having an oxygen radical attached thereto. Representative alkoxyl groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_1$, where m and $R_1$ are described below.

The terms "amine" and "amino" are art-recognized and refer to both unsubstituted and substituted amines, e.g., a moiety that can be represented by the general formulae:

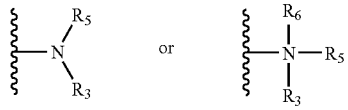

wherein $R_3$, $R_5$ and $R_6$ each independently represent a hydrogen, an alkyl, an alkenyl, —$(CH_2)_m$—$R_1$, or $R_3$ and $R_5$ taken together with the N atom to which they are attached complete a heterocycle having from 4 to 8 atoms in the ring structure; $R_1$ represents an alkenyl, aryl, cycloalkyl, a cycloalkenyl, a heterocyclyl or a polycyclyl; and m is zero or an integer in the range of 1 to 8. In preferred embodiments, only one of $R_3$ or $R_5$ can be a carbonyl, e.g., $R_3$, $R_5$ and the nitrogen together do not form an imide. In even more preferred embodiments, $R_3$ and $R_5$ (and optionally $R_6$) each independently represent a hydrogen, an alkyl, an alkenyl, or —$(CH_2)_m$—$R_1$. Thus, the term "alkylamine" as used herein means an amine group, as defined above, having a substituted or unsubstituted alkyl attached thereto, i.e., at least one of $R_3$ and $R_5$ is an alkyl group. In certain embodiments, an amino group or an alkylamine is basic, meaning it has a $pK_a \geq 7.00$. The protonated forms of these functional groups have $pK_a$s relative to water above 7.00.

The term "carbonyl" is art-recognized and includes such moieties as can be represented by the general formula:

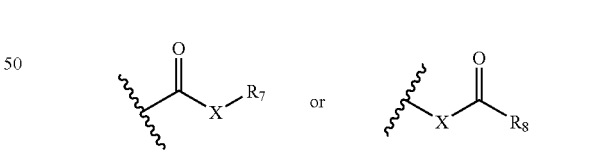

wherein X is a bond or represents an oxygen or a sulfur, and $R_7$ represents a hydrogen, an alkyl, an alkenyl, —$(CH_2)_m$—$R_1$ or a pharmaceutically acceptable salt, $R_8$ represents a hydrogen, an alkyl, an alkenyl or —$(CH_2)_m$—$R_1$, where m and $R_1$ are as defined above. Where X is an oxygen and $R_7$ or $R_8$ is not hydrogen, the formula represents an "ester". Where X is an oxygen, and $R_7$ is as defined above, the moiety is referred to herein as a carboxyl group, and particularly when $R_7$ is a hydrogen, the formula represents a "carboxylic acid". Where X is an oxygen, and $R_8$ is hydrogen, the formula represents a "formate". In general, where the oxygen atom of the above formula is replaced by sulfur, the formula represents a "thiocarbonyl" group. Where X is a sulfur and $R_7$ or $R_8$ is not hydrogen, the formula represents a "thioester" group. Where X is a sulfur and $R_7$ is hydrogen, the formula represents a "thiocarboxylic acid" group. Where X is a sulfur and $R_8$ is hydrogen, the formula represents a "thioformate" group. On the other hand, where X is a bond, and $R_7$ is not hydrogen, the above formula represents a "ketone" group. Where X is a bond, and $R_7$ is hydrogen, the above formula represents an "aldehyde" group.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, sulfamoyl, sulfinyl, ether, alkylthio, sulfonyl, ketone, aldehyde, ester, a heterocyclyl, an aromatic or heteroaromatic moiety, —$CF_3$, —CN, or the like.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The term "hydrocarbyl" refers to a monovalent hydrocarbon radical comprised of carbon chains or rings of up to 26 carbon atoms to which hydrogen atoms are attached. The term includes alkyl, cycloalkyl, alkenyl, alkynyl and aryl groups, groups which have a mixture of saturated and unsaturated bonds, carbocyclic rings and includes combinations of such groups. It may refer to straight chain, branched-chain, cyclic structures or combinations thereof.

The term "hydrocarbylene" refers to a divalent hydrocarbyl radical. Representative examples include alkylene, phenylene, or cyclohexylene. Preferably, the hydrocarbylene chain is fully saturated and/or has a chain of 1–10 carbon atoms.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

The term "sulfamoyl" is art-recognized and includes a moiety that can be represented by the general formula:

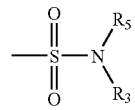

in which $R_3$ and $R_5$ are as defined above.

The term "sulfate" is art recognized and includes a moiety that can be represented by the general formula:

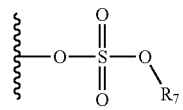

in which $R_7$ is as defined above.

The term "sulfonamido" is art recognized and includes a moiety that can be represented by the general formula:

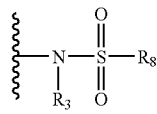

in which $R_2$ and $R_4$ are as defined above.

The term "sulfonate" is art-recognized and includes a moiety that can be represented by the general formula:

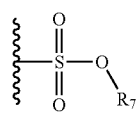

in which $R_7$ is an electron pair, hydrogen, alkyl, cycloalkyl, or aryl.

The terms "sulfoxido" or "sulfinyl", as used herein, refers to a moiety that can be represented by the general formula:

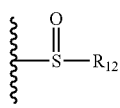

in which $R_{12}$ is selected from the group consisting of hydrogen, alkyl, alkenyl, alkynyl, cycloalkyl, heterocyclyl, aralkyl, or aryl.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g., alkyl, m, n, etc., when it occurs more than once in any structure, is intended to be independent of its definition elsewhere in the same structure.

A "small" substituent is one of 10 atoms or less.

By the terms "amino acid residue" and "peptide residue" is meant an amino acid or peptide molecule without the —OH of its carboxyl group. In general the abbreviations used herein for designating the amino acids and the protective groups are based on recommendations of the IUPAC-IUB Commission on Biochemical Nomenclature (see Biochemistry (1972) 11:1726–1732). For instance Met, Ile, Leu, Ala and Gly represent "residues" of methionine, isoleucine, leucine, alanine and glycine, respectively. By the residue is meant a radical derived from the corresponding α-amino acid by eliminating the OH portion of the carboxyl group and the H portion of the α-amino group. The term "amino acid side chain" is that part of an amino acid exclusive of the —CH(NH$_2$)COOH portion, as defined by K. D. Kopple, "Peptides and Amino Acids", W. A. Benjamin Inc., New York and Amsterdam, 1966, pages 2 and 33; examples of such side chains of the common amino acids are —CH$_2$CH$_2$SCH$_3$ (the side chain of methionine), —CH$_2$(CH$_3$)—CH$_2$CH$_3$ (the side chain of isoleucine), —CH$_2$CH(CH$_3$)$_2$ (the side chain of leucine) or H— (the side chain of glycine).

For the most part, the amino acids used in the application of this invention are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan, and those amino acids and amino acid analogs which have been identified as constituents of peptidylglycan bacterial cell walls.

The term amino acid residue further includes analogs, derivatives and congeners of any specific amino acid referred to herein, as well as C-terminal or N-terminal protected amino acid derivatives (e.g. modified with an N-terminal or C-terminal protecting group). For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups). For instance, the subject compound can include an amino acid analog such as, for example, cyanoalanine, canavanine, djenkolic acid, norleucine, 3-phosphoserine, homoserine, dihydroxy-phenylalanine, 5-hydroxytryptophan, 1-methylhistidine, 3-methylhistidine, diaminopimelic acid, ornithine, or diaminobutyric acid. Other naturally occurring amino acid metabolites or precursors having side chains which are suitable herein will be recognized by those skilled in the art and are included in the scope of the present invention.

Also included are the (D) and (L) stereoisomers of such amino acids when the structure of the amino acid admits of stereoisomeric forms. The configuration of the amino acids and amino acid residues herein are designated by the appropriate symbols (D), (L) or (DL), furthermore when the configuration is not designated the amino acid or residue can have the configuration (D), (L) or (DL). It will be noted that the structure of some of the compounds of this invention includes asymmetric carbon atoms. It is to be understood accordingly that the isomers arising from such asymmetry are included within the scope of this invention. Such isomers can be obtained in substantially pure form by classical separation techniques and by sterically controlled synthesis. For the purposes of this application, unless expressly noted to the contrary, a named amino acid shall be construed to include both the (D) or (L) stereoisomers.

The phrase "protecting group" as used herein means substituents which protect the reactive functional group from undesirable chemical reactions. Examples of such protecting groups include esters of carboxylic acids and boronic acids, ethers of alcohols and acetals and ketals of aldehydes and ketones. For instance, the phrase "N-terminal protecting group" or "amino-protecting group" as used herein refers to various amino-protecting groups which can be employed to protect the N-terminus of an amino acid or peptide against undesirable reactions during synthetic procedures. Examples of suitable groups include acyl protecting groups such as, to illustrate, formyl, dansyl, acetyl, benzoyl, trifluoroacetyl, succinyl and methoxysuccinyl; aromatic urethane protecting groups as, for example, benzyloxycarbonyl (Cbz); and aliphatic urethane protecting groups such as t-butoxycarbonyl (Boc) or 9-Fluorenylmethoxycarbonyl (FMOC).

As noted above, certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and non-aromatic organic compounds which can be substituted or unsubstituted.

A compound is said to have an "insulinotropic activity" if it is able to stimulate, or cause the stimulation of, the synthesis or expression of the hormone insulin.

It will be understood that all generic structures recited herein, with respect to appropriate combinations of substituents, are intended to cover those embodiments permited by valency and stability.

III. Exemplary Embodiments (i). Compounds

One aspect of the present invention is a compound represented by Formula I:

19

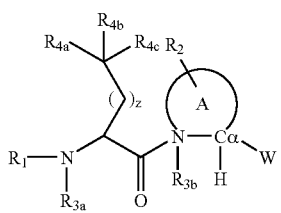

wherein

A represents a 3–8 membered heterocycle including the N and the Cα carbon;

W represents a functional group which reacts with an active site residue of the targeted protease to form a covalent adduct, as for example, —CN, —CH=NR$_5$,

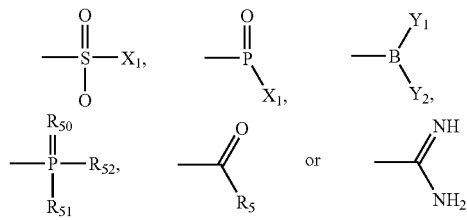

R$_1$ represents a hydrogen, a C-terminally linked amino acid or peptide or analog thereof, or amino protecting group;

R$_2$ is absent or represents one or more substitutions to the ring A, each of which can independently be a halogen, a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, a nitro, an azido, a sulfate, a sulfonate, a sulfonamido, —(CH$_2$)$_m$—R$_6$, —(CH$_2$)$_m$—OH, —(CH$_2$)$_m$—O-lower alkyl, —(CH$_2$)$_m$—O-lower alkenyl, —(CH$_2$)$_n$—O—(CH$_2$)$_m$—R$_6$, —(CH$_2$)$_m$—SH, —(CH$_2$)$_m$—S-lower alkyl, —(CH$_2$)$_m$—S-lower alkenyl, —(CH$_2$)$_n$—S—(CH$_2$)$_m$—R$_6$;

R$_{3a}$ represents a hydrogen or a substituent which does not conjugate the electron pair of the nitrogen from which it pends, such as a lower alkyl;

R$_{3b}$ is absent, or represents a substituent which does not conjugate the electron pair of the nitrogen from which it pends, such as a lower alkyl;

R$_{4a}$ and R$_{4b}$ each independently represent a hydrogen, lower alkyl, heteroalkyl, cycloalkyl, heterocycloalkyl, aryl, heteroaryl, alkoxyl, carboxyl, carboxamide, carbonyl, or cyano, with the caveat that either both or neither of R$_{4a}$ and R$_{4b}$ are hydrogen;

R$_{4c}$ represents a halogen, an amine, an alkyl, heteroalkyl, cycloalkyl, heterocycloalkyl, aryl, heteroaryl, alkoxyl, carboxyl, carboxamide, carbonyl, or cyano;

R$_5$ represents H, an alkyl, an alkenyl, an alkynyl, —C(X$_1$)(X$_2$)X$_3$, —(CH$_2$)m-R$_6$, —(CH$_2$)n-OH, —(CH$_2$)n-O-alkyl, —(CH$_2$)n-O-alkenyl, —(CH$_2$)n-O-alkynyl, —(CH$_2$)n-O—(CH$_2$)m-R$_6$, —(CH$_2$)n-SH, —(CH$_2$)n-S-alkyl, —(CH$_2$)n-S-alkenyl, —(CH$_2$)n-S-alkynyl, —(CH$_2$)n-S—(CH$_2$)m-R$_6$, —C(O)C(O)NH$_2$, —C(O)C(O)OR$_7$;

R$_6$ represents, independently for each occurrence, an aryl, aralkyl, cycloalkyl, cycloalkenyl, or heterocycle moiety;

R$_7$ represents, independently for each occurrence, hydrogen, or an alkyl, alkenyl, aryl, aralkyl, cycloalkyl, cycloalkenyl, or heterocycle moiety; and

20

Y$_1$ and Y$_2$ each independently represent —OH, or a group capable of being hydrolyzed to a hydroxyl group, including cyclic derivatives where Y$_1$ and Y$_2$ are connected via a ring having from 5 to 8 atoms in the ring structure (such as pinacol or the like), R$_{50}$ represents O or S;

R$_{51}$ represents N$_3$, SH$_2$, NH$_2$, NO$_2$ or —OR$_7$;

R$_{52}$ represents hydrogen, a lower alkyl, an amine, —OR$_7$, or a pharmaceutically acceptable salt, or R$_{51}$ and R$_{52}$ taken together with the phosphorous atom to which they are attached complete a heterocyclic ring having from 5 to 8 atoms in the ring structure X$_1$ represents a halogen;

X$_2$ and X$_3$ each represent a hydrogen or a halogen;

z is zero or an integer in the range of 1 to 3 (preferably 0 or 1); m is zero or an integer in the range of 1 to 8; and n is an integer in the range of 1 to 8.

In certain embodiments, the protease inhibitor is represented in the general formula II:

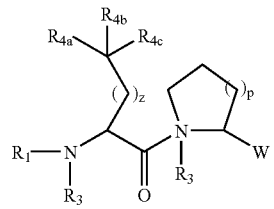

where R$_1$, R$_{3a}$, R$_{3b}$, R$_{4a}$, R$_{4b}$, R$_{4c}$ and W are as defined above, and p is an integer from 1 to 3. In certain preferred embodiments, p is 1, and R$_{3a}$ is a hydrogen and R$_{3b}$ is absent.

Another aspect of the present invention is a compound represented by Formula III:

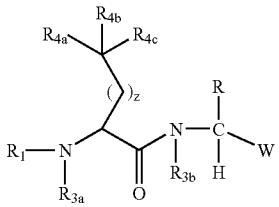

wherein

R represents hydrogen, a halogen, or a branched or unbranched C1–C6 alkyl which is unsubstituted or substituted with one or more of —OH, —SH, —NH$_2$ or a halogen;

W represents a functional group which reacts with an active site residue of the targeted protease to form a covalent adduct, as for example, —CN, —CH=NR$_5$,

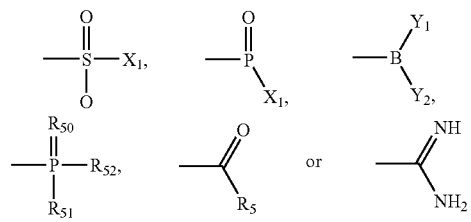

R$_1$ represents a hydrogen, a C-terminally linked amino acid or peptide or analog thereof, or amino protecting group;

$R_{3a}$ represents a hydrogen or a substituent which does not conjugate the electron pair of the nitrogen from which it pends, such as a lower alkyl;

$R_{3b}$ is absent, or represents a substituent which does not conjugate the electron pair of the nitrogen from which it pends, such as a lower alkyl;

$R_{4a}$ and $R_{4b}$ each independently represent a hydrogen, lower alkyl, heteroalkyl, cycloalkyl, heterocycloalkyl, aryl, heteroaryl, alkoxyl, carboxyl, carboxamide, carbonyl, or cyano, with the caveat that either both or neither of $R_{4a}$ and $R_{4b}$ are hydrogen;

$R_{4c}$ represents a halogen, an amine, an alkyl, heteroalkyl, cycloalkyl, heterocycloalkyl, aryl, heteroaryl, alkoxyl, carboxyl, carboxamide, carbonyl, or cyano;

$R_5$ represents H, an alkyl, an alkenyl, an alkynyl, —C($X_1$)($X_2$)$X_3$, —(CH$_2$)m-$R_6$, —(CH$_2$)n-OH, —(CH$_2$)n-O-alkyl, —(CH$_2$)n-O-alkenyl, —(CH$_2$)n-O-alkynyl, —(CH$_2$)n-O—(CH$_2$)m-$R_6$, —(CH$_2$)n-SH, —(CH$_2$)n-S-alkyl, —(CH$_2$)n-S-alkenyl, —(CH$_2$)n-S-alkynyl, —(CH$_2$)n-S—(CH$_2$)m-$R_6$, —C(O)C(O)NH$_2$, —C(O)C(O)O$R_7$;

$R_6$ represents, independently for each occurrence, an aryl, aralkyl, cycloalkyl, cycloalkenyl, or heterocycle moiety;

$R_7$ represents, independently for each occurrence, hydrogen, or an alkyl, alkenyl, aryl, aralkyl, cycloalkyl, cycloalkenyl, or heterocycle moiety; and $Y_1$ and $Y_2$ each independently represent —OH, or a group capable of being hydrolyzed to a hydroxyl group, including cyclic derivatives where $Y_1$ and $Y_2$ are connected via a ring having from 5 to 8 atoms in the ring structure (such as pinacol or the like), $R_{50}$ represents O or S;

$R_{51}$ represents N$_3$, SH$_2$, NH$_2$, NO$_2$ or —O$R_7$;

$R_{52}$ represents hydrogen, a lower alkyl, an amine, —O$R_7$, or a pharmaceutically acceptable salt, or $R_{51}$ and $R_{52}$ taken together with the phosphorous atom to which they are attached complete a heterocyclic ring having from 5 to 8 atoms in the ring structure $X_1$ represents a halogen;

$X_2$ and $X_3$ each represent a hydrogen or a halogen;

z is zero or an integer in the range of 1 to 3 (preferably 0 or 1); m is zero or an integer in the range of 1 to 8; and n is an integer in the range of 1 to 8.

Yet another aspect of the present invention provides a compound represented by Formula IV:

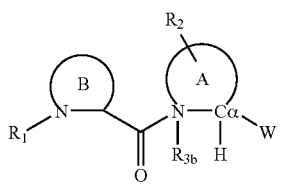

wherein

A represents a 3–8 membered heterocycle including the N and the Cα carbon;

B represents a C3–C8 ring, or C7–C14 fused bicyclic or tricyclic ring system;

W represents a functional group which reacts with an active site residue of the targeted protease to form a covalent adduct, as for example, —CN, —CH=N$R_5$,

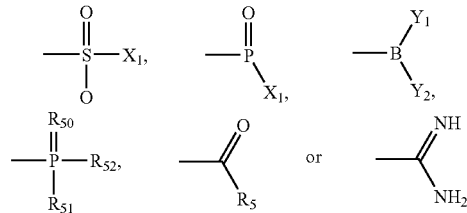

$R_1$ represents a hydrogen, a C-terminally linked amino acid or peptide or analog thereof, or amino protecting group;

$R_2$ is absent or represents one or more substitutions to the ring A, each of which can independently be a halogen, a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, a nitro, an azido, a sulfate, a sulfonate, a sulfonamido, —(CH$_2$)$_m$—$R_6$, —(CH$_2$)$_m$—OH, —(CH$_2$)$_m$—O-lower alkyl, —(CH$_2$)$_m$—O-lower alkenyl, —(CH$_2$)$_n$—O—(CH$_2$)$_m$—$R_6$, —(CH$_2$)$_m$—SH, —(CH$_2$)$_m$—S-lower alkyl, —(CH$_2$)$_m$—S-lower alkenyl, —(CH$_2$)$_n$—S—(CH$_2$)$_m$—$R_6$;

$R_{3b}$ is absent, or represents a substituent which does not conjugate the electron pair of the nitrogen from which it pends, such as a lower alkyl;

$R_5$ represents H, an alkyl, an alkenyl, an alkynyl, —C($X_1$)($X_2$)$X_3$, —(CH$_2$)m-$R_6$, —(CH$_2$)n-OH, —(CH$_2$)n-O-alkyl, —(CH$_2$)n-O-alkenyl, —(CH$_2$)n-O-alkynyl, —(CH$_2$)n-O—(CH$_2$)m-$R_6$, —(CH$_2$)n-SH, —(CH$_2$)n-S-alkyl, —(CH$_2$)n-S-alkenyl, —(CH$_2$)n-S-alkynyl, —(CH$_2$)n-S—(CH$_2$)m-$R_6$, —C(O)C(O)NH$_2$, —C(O)C(O)O$R_7$;

$R_6$ represents, independently for each occurrence, an aryl, aralkyl, cycloalkyl, cycloalkenyl, or heterocycle moiety;

$R_7$ represents, independently for each occurrence, hydrogen, or an alkyl, alkenyl, aryl, aralkyl, cycloalkyl, cycloalkenyl, or heterocycle moiety; and $Y_1$ and $Y_2$ each independently represent —OH, or a group capable of being hydrolyzed to a hydroxyl group, including cyclic derivatives where $Y_1$ and $Y_2$ are connected via a ring having from 5 to 8 atoms in the ring structure (such as pinacol or the like), $R_{50}$ represents O or S;

$R_{51}$ represents N$_3$, SH$_2$, NH$_2$, NO$_2$ or —O$R_7$;

$R_{52}$ represents hydrogen, a lower alkyl, an amine, —O$R_7$, or a pharmaceutically acceptable salt, or $R_{51}$ and $R_{52}$ taken together with the phosphorous atom to which they are attached complete a heterocyclic ring having from 5 to 8 atoms in the ring structure $X_1$ represents a halogen;

$X_2$ and $X_3$ each represent a hydrogen or a halogen;

m is zero or an integer in the range of 1 to 8; and n is an integer in the range of 1 to 8.

In certain embodiments, the protease inhibitor is represented in the general formula V:

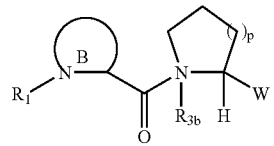

where B, $R_1$, $R_{3b}$ and W are as defined above, and p is an integer from 1 to 3. In certain preferred embodiments, p is 1, and $R_{3a}$ is a hydrogen and $R_{3b}$ is absent.

Another aspect of the present invention is a compound represented by Formula VI:

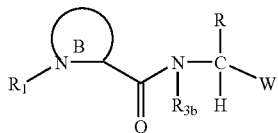

R represents hydrogen, a halogen, or a branched or unbranched C1–C6 alkyl which is unsubstituted or substituted with one or more of —H, —SH, —NH$_2$ or a halogen;

B represents a C3–C8 ring, or C7–C14 fused bicyclic or tricyclic ring system;

W represents a functional group which reacts with an active site residue of the targeted protease to form a covalent adduct, as for example, —CN, —CH=NR$_5$,

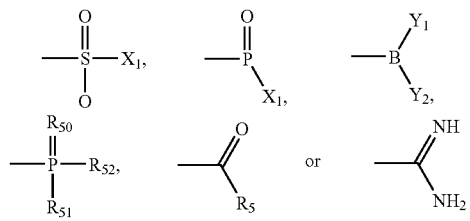

$R_1$ represents a hydrogen, a C-terminally linked amino acid or peptide or analog thereof, or amino protecting group;

$R_{3b}$ is absent, or represents a substituent which does not conjugate the electron pair of the nitrogen from which it pends, such as a lower alkyl;

$R_5$ represents H, an alkyl, an alkenyl, an alkynyl, —C(X$_1$)(X$_2$)X$_3$, —(CH$_2$)m-R$_6$, —(CH$_2$)n-OH, —(CH$_2$)n-O-alkyl, —(CH$_2$)n-O-alkenyl, —(CH$_2$)n-O-alkynyl, —(CH$_2$)n-O-(CH$_2$)m-R$_6$, —(CH$_2$)n-SH, —(CH$_2$)n-S-alkyl, —(CH$_2$)n-S-alkenyl, —(CH$_2$)n-S-alkynyl, —(CH$_2$)n-S—(CH$_2$)m-R$_6$, —C(O)C(O)NH$_2$, —C(O)C(O)OR$_7$;

$R_6$ represents, independently for each occurrence, an aryl, aralkyl, cycloalkyl, cycloalkenyl, or heterocycle moiety;

$R_7$ represents, independently for each occurrence, hydrogen, or an alkyl, alkenyl, aryl, aralkyl, cycloalkyl, cycloalkenyl, or heterocycle moiety; and $Y_1$ and $Y_2$ each independently represent —OH, or a group capable of being hydrolyzed to a hydroxyl group, including cyclic derivatives where $Y_1$ and $Y_2$ are connected via a ring having from 5 to 8 atoms in the ring structure (such as pinacol or the like), $R_{50}$ represents O or S;

$R_{51}$ represents N$_3$, SH$_2$, NH$_2$, NO$_2$ or —OR$_7$;

$R_{52}$ represents hydrogen, a lower alkyl, an amine, —OR$_7$, or a pharmaceutically acceptable salt, or $R_{51}$ and $R_{52}$ taken together with the phosphorous atom to which they are attached complete a heterocyclic ring having from 5 to 8 atoms in the ring structure $X_1$ represents a halogen;

$X_2$ and $X_3$ each represent a hydrogen or a halogen;

m is zero or an integer in the range of 1 to 8; and n is an integer in the range of 1 to 8.

In certain preferred embodiments of the subject inhibitor structures above, W represents:

In certain preferred embodiments of the subject inhibitor structures above, $R_5$ is a hydrogen or —C(X$_1$)(X$_2$)X$_3$, wherein $X_1$ is a fluorine, and $X_2$ and $X_3$, if halogens, are also fluorine.

In certain preferred embodiments of the subject inhibitor structures above, $R_1$ is a peptidyl moiety which is a substrate for a protease which cleaves between $R_1$ and its pendent amine moiety. In other preferred embodiments, $R_1$ is an amino blocking group.

In certain preferred embodiments, A is a 4–8 membered ring, more preferably a 5, 6 or 7 membered ring. A can be a ring selected from the group consisting of azaridines, thiazoles, pyrroles, diazoles (such as imidazoles and pyrazolidines), pyridines, oxazoles, isozazoles, isothiazoles, azepines, diazepines, oxadiazoles, oxatriazoles, dioxazoles, oxathiazoles, pyrimidines, pyridazines, pyranzines, triazines, oxazines, isoxzaines, and oxathiazines, or reduced forms thereof (e.g., dihydro- and tetrahydro-versions thereof), such pyrrolidines, piperidines, piperazines, morpholines, thiazolidines, and imidazolines.

In certain preferred embodiments, A is a thiazole, pyrrole, or pyridine, or reduced form thereof.

In certain preferred embodiments, R represents hydrogen or a branched or unbranched C1–C6 alkyl;

In certain preferred embodiments, $R_2$ is absent. In other preferred embodiments, $R_2$ represents one or two, preferably one, hydroxyl group.

In certain preferred embodiments, $R_{3a}$ and $R_{3b}$ each independently represent hydrogen. In other preferred embodiments, $R_{3a}$ and $R_{3b}$ each independently represent hydrogen or a C1–C3 alkyl.

In certain preferred embodiments, each of $R_{4a}$ and $R_{4b}$ each independently represent (subject to the above proviso) hydrogen or a small hydrophobic group such as a halogen, a lower alkyl, a lower alkenyl, or a lower alkynyl; and $R_{4c}$ represents a halogen, a lower alkyl, a lower alkenyl, or a lower alkynyl. In certain preferred embodiments, $R_{4a}$ is a hydrogen, and $R_{4b}$ and $R_{4c}$ are both C1–4 alkyls, or $R_{4a}$, $R_{4b}$ and $R_{4c}$ are all C1–4 alkyls.

In certain preferred embodiments, $R_{4a}$ and $R_{4b}$ are both hydrogen, and $R_{4c}$ represents a cycloalkyl, a heterocycloalkyl, an aryl or heteroaryl group, such as a 3–8 membered ring, more preferably a 5, 6 or 7 membered ring. The ring may be substituted by up to 4 heteroatoms—selected from the group consisting of O (oxygen), S (sulphur) or N (nitrogen). In certain preferred embodiments, $R_{4c}$ is a cycloalkyl.

In certain embodiments, B is 3–8 membered ring, more preferably a 5, 6 or 7 membered ring. B can be a ring selected from the group consisting of azaridines, thiazoles, pyrroles, diazoles (such as imidazoles and pyrazolidines), pyridines, oxazoles, isozazoles, isothiazoles, azepines, diazepines, oxadiazoles, oxatriazoles, dioxazoles, oxathiazoles, pyrimidines, pyridazines, pyranzines, triazines, oxazines, isoxzaines, and oxathiazines, or reduced forms thereof (e.g., dihydro- and tetrahydro-versions thereof), such pyrrolidines, piperidines, piperazines, morpholines, thiazolidines, and imidazolines.

In certain embodiments, B is a bicyclic or tricyclic ring such as an indole, an indolenine, an isobenzazole, a pyrindine, a pyrannopyrrole, an isoindazole, an indoxazine, a benzoxazole, an anthanil, a quinoline, an isoquinoline, a cinnoline, a quinazoline, a napthyridine, a pyridopyridine, a benzoxazine, a benzisoxazine, a carbazole, an acridine, or a purine, or reduced forms thereof (e.g., dihydro- and tetrahydro-versions thereof). In certain preferred embodiments, B is a tetrahydroisoquinoline or a tetrahydrocarboline (such as a β or γ-carboline).

In certain embodiments, B is unsubstituted, or is substituted with one or more of—OH, —SH, —NH$_2$, halogens, or lower alkyl. In certain preferred embodiments, B is unsubstituted.

In certain embodiments, B is 3–8 membered ring, more preferably a 5, 6 or 7 membered ring. B can be a ring selected from the group consisting of azaridines, thiazoles, pyrroles, diazoles (such as imidazoles and pyrazolidines), pyridines, oxazoles, isozazoles, isothiazoles, azepines, diazepines, oxadiazoles, oxatriazoles, dioxazoles, oxathiazoles, pyrimidines, pyridazines, pyranzines, triazines, oxazines, isoxzaines, and oxathiazines, or reduced forms thereof (e.g., dihydro- and tetrahydro-versions thereof), such pyrrolidines, piperidines, piperazines, morpholines, thiazolidines, and imidazolines.

In certain embodiments, B is a bicyclic or tricyclic ring such as an indole, an indolenine, an isobenzazole, a pyrindine, a pyrannopyrrole, an isoindazole, an indoxazine, a benzoxazole, an anthanil, a quinoline, an isoquinoline, a cinnoline, a quinazoline, a napthyridine, a pyridopyridine, a benzoxazine, a benzisoxazine, a carbazole, an acridine, or a purine, or reduced forms thereof (e.g., dihydro- and tetrahydro-versions thereof). In certain preferred embodiments, B is a tetrahydroisoquinoline or a tetrahydrocarboline (such as a β or γ-carboline).

In certain preferred embodiments, if A represents a pyrrolidine ring, then R$_{4a}$, R$_{4b}$ and R$_{4c}$ are selected such that they do not give rise to a naturally occurring amino acid side chain, e.g., as defined by the IUPAC-IUB Commission on Biochemical Nomenclature.

In certain preferred embodiments, if R$_{4a}$, R$_{4b}$ and R$_{4c}$ are selected to give rise to a naturally occurring amino acid side chain, e.g., as defined by the IUPAC-IUB Commission on Biochemical Nomenclature, then A is not a pyrrolidine ring.

In certain preferred embodiments, z is zero or 1.

Exemplary structures include compounds include.

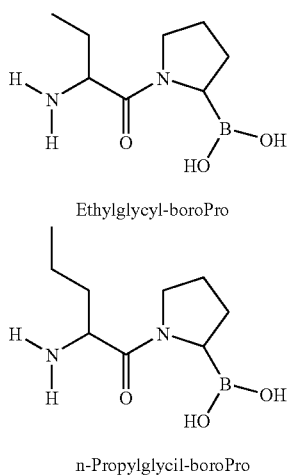

Ethylglycyl-boroPro n-Propylglycil-boroPro

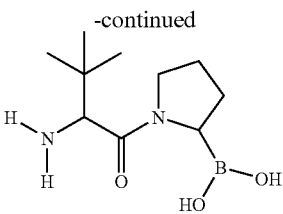

t-Butyl-boroPro

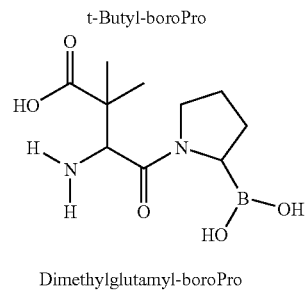

Dimethylglutamyl-boroPro

In certain preferred embodiments, the subject inhibitors are DPIV inhibitors with a Ki for DPIV inhibition of 10 nm or less, more preferably of 1.0 nm or less, and even more preferably of 0.1 or even 0.01 nM or less. Indeed, inhibitors with Ki values in the picomolar and even femtomolar range are contemplated.

In general, the inhibitors of the subject method will be small molecules, e.g., with molecular weights less than 7500 amu, preferably less than 5000 amu, and even more preferably less than 2000 amu and even 1000 amu. In preferred embodiments, the inhibitors will be orally active.

Another aspect of the present invention relates to pharmaceutical compositions of dipeptidylpeptidase inhibitors, particularly inhibitor(s), and their uses in treating and/or preventing disorders which can be improved by altering the homeostasis of peptide hormones. In a preferred embodiment, the inhibitors have hypoglycemic and antidiabetic activities, and can be used in the treatment of disorders marked by abberrant glucose metabolism (including storage). In particular embodiments, the compositions of the subject methods are useful as insulinotropic agents, or to potentiate the insulinotropic effects of such molecules as GLP-1. In this regard, the present method can be useful for the treatment and/or prophylaxis of a variety of disorders, including one or more of: hyperlipemia, hyperglycemia, obesity, glucose tolerance insufficiency, insulin resistance and diabetic complications.

For instance, in certain embodiments the method involves administration of an inhibitor(s), preferably at a predetermined time(s) during a 24-hour period, in an amount effective to improve one or more aberrant indices associated with glucose metabolism disorders (e.g., glucose intolerance, insulin resistance, hyperglycemia, hyperinsulinemia and Type II diabetes). The effective amount of the inhibitor may be about 0.01, 0.1, 1, 10, 30, 50, 70, 100, 150, 200, 500, or 1000 mg/kg of the subject.

(ii). Agonism of GLP-1 Effects

The inhibitors useful in the subject methods possess, in certain embodiments, the ability to lower blood glucose levels, to relieve obesity, to alleviate impaired glucose tolerance, to inhibit hepatic glucose neogenesis, and to lower blood lipid levels and to inhibit aldose reductase. They are thus useful for the prevention and/or therapy of hyperglycemia, obesity, hyperlipidemia, diabetic complications (including retinopathy, nephropathy, neuropathy, cataracts, coronary artery disease and arteriosclerosis) and furthermore for obesity-related hypertension and osteoporosis.

Diabetes mellitus is a disease characterized by hyperglycemia occurring from a relative or absolute decrease in insulin secretion, decreased insulin sensitivity or insulin resistance. The morbidity and mortality of this disease result from vascular, renal, and neurological complications. An oral glucose tolerance test is a clinical test used to diagnose diabetes. In an oral glucose tolerance test, a patient's physiological response to a glucose load or challenge is evaluated. After ingesting the glucose, the patient's physiological response to the glucose challenge is evaluated. Generally, this is accomplished by determining the patient's blood glucose levels (the concentration of glucose in the patient's plasma, serum or whole blood) for several predetermined points in time.

In one embodiment, the present invention provides a method for agonizing the action of GLP-1. It has been determined that isoforms of GLP-1(GLP-1(7–37) and GLP-1 (7–36)), which are derived from preproglucagon in the intestine and the hind brain, have insulinotropic activity, i.e., they modulate glucose metabolism. DPIV cleaves the isoforms to inactive peptides. Thus, in certain embodiments, inhibitor(s) of the present invention can agonize insulinotropic activity by interfering with the degradation of bioactive GLP-1 peptides.

(iii). Agonism of the Effects of Other Peptide Homones

In another embodiment, the subject agents can be used to agonize (e.g., mimic or potentiate) the activity of peptide hormones, e.g., GLP-2, GIP and NPY.

To illustrate further, the present invention provides a method for agonizing the action of GLP-2. It has been determined that GLP-2 acts as a trophic agent, to promote growth of gastrointestinal tissue. The effect of GLP-2 is marked particularly by increased growth of the small bowel, and is therefore herein referred to as an "intestinotrophic" effect. DPIV is known to cleave GLP-2 into a biologically inactive peptide. Thus, in one embodiment, inhibition of DPIV interferes with the degradation of GLP-2, and thereby increases the plasma half-life of that hormone.

In still other embodiments, the subject method can be used to increase the half-life of other proglucagon-derived peptides, such as glicentin, oxyntomodulin, glicentin-related pancreatic polypeptide (GRPP), and/or intervening peptide-2 (IP-2). For example, glicentin has been demonstrated to cause proliferation of intestinal mucosa and also inhibits a peristalsis of the stomach, and has thus been elucidated as useful as a therapeutic agent for digestive tract diseases, thus leading to the present invention.

Thus, in one aspect, the present invention relates to therapeutic and related uses of inhibitor(s) for promoting the growth and proliferation of gastrointestinal tissue, most particularly small bowel tissue. For instance, the subject method can be used as part of a regimen for treating injury, inflammation or resection of intestinal tissue, e.g., where enhanced growth and repair of the intestinal mucosal epithelial is desired.

With respect to small bowel tissue, such growth is measured conveniently as a increase in small bowel mass and length, relative to an untreated control. The effect of subject inhibitors on small bowel also manifests as an increase in the height of the crypt plus villus axis. Such activity is referred to herein as an "intestinotrophic" activity. The efficacy of the subject method may also be detectable as an increase in crypt cell proliferation and/or a decrease in small bowel epithelium apoptosis. These cellular effects may be noted most significantly in relation to the jejunum, including the distal jejunum and particularly the proximal jejunum, and also in the distal ileum. A compound is considered to have "intestinotrophic effect" if a test animal exhibits significantly increased small bowel weight, increased height of the crypt plus villus axis, or increased crypt cell proliferation or decreased small bowel epithelium apoptosis when treated with the compound (or genetically engineered to express it themselves). A model suitable for determining such gastrointestinal growth is described by U.S. Pat. No. 5,834,428.

In general, patients who would benefit from either increased small intestinal mass and consequent increased small bowel mucosal function are candidates for treatment by the subject method. Particular conditions that may be treated include the various forms of sprue including celiac sprue which results from a toxic reaction to □-gliadin from wheat, and is marked by a tremendous loss of villae of the bowel; tropical sprue which results from infection and is marked by partial flattening of the villae; hypogammaglobulinemic sprue which is observed commonly in patients with common variable immunodeficiency or hypogammaglobulinemia and is marked by significant decrease in villus height. The therapeutic efficacy of the treatment may be monitored by enteric biopsy to examine the villus morphology, by biochemical assessment of nutrient absorption, by patient weight gain, or by amelioration of the symptoms associated with these conditions. Other conditions that may be treated by the subject method, or for which the subject method may be useful prophylactically, include radiation enteritis, infectious or post-infectious enteritis, regional enteritis (Crohn's disease), small intestinal damage due to toxic or other chemotherapeutic agents, and patients with short bowel syndrome.

More generally, the present invention provides a therapeutic method for treating digestive tract diseases. The term "digestive tract" as used herein means a tube through which food passes, including stomach and intestine. The term "digestive tract diseases" as used herein means diseases accompanied by a qualitative or quantitative abnormality in the digestive tract mucosa, which include, e.g., ulceric or inflammatory disease; congenital or acquired digestion and absorption disorder including malabsorption syndrome; disease caused by loss of a mucosal barrier function of the gut; and protein-losing gastroenteropathy. The ulceric disease includes, e.g., gastric ulcer, duodenal ulcer, small intestinal ulcer, colonic ulcer and rectal ulcer. The inflammatory disease include, e.g., esophagitis, gastritis, duodenitis, enteritis, colitis, Crohn's disease, proctitis, gastrointestinal Behcet, radiation enteritis, radiation colitis, radiation proctitis, enteritis and medicanentosa. The malabsorption syndrome includes the essential malabsorption syndrome such as disaccharide-decomposing enzyme deficiency, glucose-galactose malabsorption, fructose malabsorption; secondary malabsorption syndrome, e.g., the disorder caused by a mucosal atrophy in the digestive tract through the intravenous or parenteral nutrition or elemental diet, the disease caused by the resection and shunt of the small intestine such as short gut syndrome, cul-de-sac syndrome; and indigestible malabsorption syndrome such as the disease caused by resection of the stomach, e.g., dumping syndrome.

The term "therapeutic agent for digestive tract diseases" as used herein means the agents for the prevention and treatment of the digestive tract diseases, which include, e.g., the therapeutic agent for digestive tract ulcer, the therapeutic agent for inflammatory digestive tract disease, the therapeutic agent for mucosal atrophy in the digestive tract and the therapeutic agent for digestive tract wound, the amelioration agent for the function of the digestive tract including the agent for recovery of the mucosal barrier function and the amelioration agent for digestive and absorptive function. The ulcers include digestive ulcers and erosions, acute ulcers, namely, acute mucosal lesions.

The subject method, because of promoting proliferation of intestinal mucosa, can be used in the treatment and prevention of pathologic conditions of insufficiency in digestion and absorption, that is, treatment and prevention of mucosal atrophy, or treatment of hypoplasia of the digestive tract tissues and decrease in these tissues by surgical removal as well as improvement of digestion and absorption. Further, the subject method can be used in the treatment of pathologic mucosal conditions due to inflammatory diseases such as enteritis, Crohn's disease and ulceric colitis and also in the treatment of reduction in function of the digestive tract after operation, for example, in damping syndrome as well as in the treatment of duodenal ulcer in conjunction with the inhibition of peristalsis of the stomach and rapid migration of food from the stomach to the jejunum. Furthermore, glicentin can effectively be used in promoting cure of surgical invasion as well as in improving functions of the digestive tract. Thus, the present invention also provides a therapeutic agent for atrophy of the digestive tract mucosa, a therapeutic agent for wounds in the digestive tract and a drug for improving functions of the digestive tract which comprise glicentin as active ingredients.

Likewise, the inhibitor(s) of the subject invention can be used to alter the plasma half-life of secretin, VIP, PHI, PACAP, GIP and/or helodermin. Additionally, the subject method can be used to alter the pharmacokinetics of Peptide YY and neuropeptide Y, both members of the pancreatic polypeptide family, as DPIV has been implicated in the processing of those peptides in a manner which alters receptor selectivity.

Neuropeptide Y (NPY) is believed to act in the regulation vascular smooth muscle tone, as well as regulation of blood pressure. NPY also decreases cardiac contractility. NPY is also the most powerful appetite stimulant known (Wilding et al., (1992) *J Endocrinology* 132:299–302). The centrally evoked food intake (appetite stimulation) effect is predominantly mediated by NPY Y1 receptors and causes increase in body fat stores and obesity (Stanley et al., (1989) *Physiology and Behavior* 46:173–177).

According to the present invention, a method for treatment of anorexia comprises administering to a host subject an effective amount of an inhibitor(s) to stimulate the appetite and increase body fat stores which thereby substantially relieves the symptoms of anorexia.

A method for treatment of hypotension comprises administering to a host subject an effective amount of an inhibitor(s) of the present invention to mediate vasoconstriction and increase blood pressure which thereby substantially relieves the symptoms of hypotension.

DPIV has also been implicated in the metabolism and inactivation of growth hormone-releasing factor (GHRF). GHRF is a member of the family of homologous peptides that includes glucagon, secretin, vasoactive intestinal peptide (VIP), peptide histidine isoleucine (PHI), pituitary adenylate cyclase activating peptide (PACAP), gastric inhibitory peptide (GIP) and helodermin. Kubiak et al. (1994) *Peptide Res* 7:153. GHRF is secreted by the hypothalamus, and stimulates the release of growth hormone (GH) from the anterior pituitary. Thus, the subject method can be used to improve clinical therapy for certain growth hormone deficient children, and in clinical therapy of adults to improve nutrition and to alter body composition (muscle vs. fat). The subject method can also be used in veterinary practice, for example, to develop higher yield milk production and higher yield, leaner livestock.

(iv). Assays of Insulinotropic Activity

In selecting a compound suitable for use in the subject method, it is noted that the insulinotropic property of a compound may be determined by providing that compound to animal cells, or injecting that compound into animals and monitoring the release of immunoreactive insulin (IRI) into the media or circulatory system of the animal, respectively. The presence of IRI can be detected through the use of a radioimmunoassay which can specifically detect insulin.

The db/db mouse is a genetically obese and diabetic strain of mouse. The db/db mouse develops hyperglycemia and hyperinsulinemia concomitant with its development of obesity and thus serves as a model of obese type 2 diabetes (NIDDM). The db/db mice can purchased from, for example, The Jackson Laboratories (Bar Harbor, Me.). In an exemplary embodiment, for treatment of the mice with a regimen including an inhibitor(s) or control, sub-orbital sinus blood samples are taken before and at some time (e.g., 60 minutes) after dosing of each animal. Blood glucose measurements can be made by any of several conventional techniques, such as using a glucose meter. The blood glucose levels of the control and inhibitor(s) dosed animals are compared.

The metabolic fate of exogenous GLP-1 can also be followed in either nondiabetic and type II diabetic subjects, and the effect of a candidate inhibitor(s) determined. For instance, a combination of high-pressure liquid chromatography (HPLC), specific radioimmunoassays (RIAs), and a enzyme-linked immunosorbent assay (ELISA), can be used, whereby intact biologically active GLP-1 and its metabolites can be detected. See, for example, Deacon et al. (1995) *Diabetes* 44:1126–1131. To illustrate, after GLP-1 administration, the intact peptide can be measured using an NH2-terminally directed RIA or ELISA, while the difference in concentration between these assays and a COOH-terminal-specific RIA allowed determination of NH2-terminally truncated metabolites. Without inhibitor, subcutaneous GLP-1 is rapidly degraded in a time-dependent manner, forming a metabolite which co-elutes on HPLC with GLP-I(9–36) amide and has the same immunoreactive profile. For instance, thirty minutes after subcutaneous GLP-1 administration to diabetic patients (n=8), the metabolite accounted for 88.5+1.9% of the increase in plasma immunoreactivity determined by the COOH-terminal RIA, which was higher than the levels measured in healthy subjects (78.4+3.2%; n=8; P<0.05). See Deacon et al., supra. Intravenously infused GLP-I was also extensively degraded.

(v). Conjoint Administration

Another aspect of the invention provides a conjoint therapy wherein one or more other therapeutic agents are administered with the protease inhibitor. Such conjoint treatment may be achieved by way of the simultaneous, sequential or separate dosing of the individual components of the treatment.

In one embodiment, an inhibitor(s) is conjointly administered with insulin or other insulinotropic agents, such as GLP-1, peptide hormones, such as GLP-2, GIP, or NPY, or a gene therapy vector which causes the ectopic expression of said agents and peptide hormones. In certain embodiments, said agents or peptide hormones may be variants of a naturally occurring or synthetic peptide hormone, wherein one or more amino acids have been added, deleted or substituted.

In another illustrative embodiment, the subject inhibitors can be conjointly administered with a an M1 receptor antagonist. Cholinergic agents are potent modulators of insulin release that act via muscarinic receptors. Moreover, the use of such agents can have the added benefit of decreasing cholesterol levels, while increasing HDL levels. Suitable muscarinic receptor antagonists include substances that directly or indirectly block activation of muscarinic cholinergic receptors. Preferably, such substances are selective (or are used in amounts that promote such selectivity) for the M1 receptor. Nonlimiting examples include quaternary amines (such as methantheline, ipratropium, and propantheline), tertiary amines (e.g. dicyclomine, scopolamine) and tricyclic amines (e.g. telenzepine). Pirenzepine and methyl scopolamine are preferred. Other suitable muscarinic receptor antagonists include benztropine (commercially available as COGENTIN from Merck), hexahydro-sila-difenidol hydrochloride (HHSID hydrochloride disclosed in Lambrecht et al. (1989) *Trends in Pharmacol. Sci.* 10(Suppl):60; (+/−)-3-quinuclidinyl xanthene-9-carboxylate hemioxalate (QNX-hemioxalate; Birdsall et al., Trends in Pharmacol. Sci. 4:459, 1983; telenzepine dihydrochloride (Coruzzi et al. (1989) *Arch. Int. Pharmacodyn. Ther.* 302:232; and Kawashima et al. (1990) *Gen. Pharmacol.* 21:17) and atropine. The dosages of such muscarinic receptor antagonists will be generally subject to optimization as outlined above. In the case of lipid metabolism disorders, dosage optimization may be necessary independently of whether administration is timed by reference to the lipid metabolism responsiveness window or not.

In terms of regulating insulin and lipid metabolism and reducing the foregoing disorders, the subject inhibitor(s) may also act synergistically with prolactin inhibitors such as d2 dopamine agonists (e.g. bromocriptine). Accordingly, the subject method can include the conjoint administration of such prolactin inhibitors as prolactin-inhibiting ergo alkaloids and prolactin-inhibiting dopamine agonists. Examples of suitable compounds include 2-bromo-alpha-ergocriptine, 6-methyl-8 beta-carbobenzyloxyaminoethyl-10-alpha-ergoline, 8-acylaminoergolines, 6-methyl-8-alpha-(N-acyl) amino-9-ergoline, 6-methyl-8-alpha-(N-phenylacetyl) amino-9-ergoline, ergocornine, 9,10-dihydroergocornine, D-2-halo-6-alkyl-8-substituted ergolines, D-2-bromo-6-methyl-8-cyanomethylergoline, carbidopa, benserazide and other dopadecarboxylase inhibitors, L-dopa, dopamine and non toxic salts thereof.

The inhibitor(s) used according to the invention can also be used conjointly with agents acting on the ATP-dependent potassium channel of the β-cells, such as glibenclamide, glipizide, gliclazide and AG-EE 623 ZW. The inhibitor(s) may also advantageously be applied in combination with other oral agents such as metformin and related compounds or glucosidase inhibitors as, for example, acarbose.

(vi). Pharmaceutical Compositions

Inhibitors prepared as described herein can be administered in various forms, depending on the disorder to be treated and the age, condition and body weight of the patient, as is well known in the art. For example, where the compounds are to be administered orally, they may be formulated as tablets, capsules, granules, powders or syrups; or for parenteral administration, they may be formulated as injections (intravenous, intramuscular or subcutaneous), drop infusion preparations or suppositories. For application by the ophthalmic mucous membrane route, they may be formulated as eyedrops or eye ointments. These formulations can be prepared by conventional means, and, if desired, the active ingredient may be mixed with any conventional additive, such as an excipient, a binder, a disintegrating agent, a lubricant, a corrigent, a solubilizing agent, a suspension aid, an emulsifying agent or a coating agent. Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses.

The precise time of administration and/or amount of the inhibitor that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically acceptable salts" refers to the relatively non-toxic, inorganic and organic acid addition salts of the inhibitor(s). These salts can be prepared in situ during the final isolation and purification of the inhibitor(s), or by separately reacting a purified inhibitor(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1–19)

In other cases, the inhibitors useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of an inhibitor(s). These salts can likewise be prepared in situ during the final isolation and purification of the inhibitor(s), or by separately reacting the purified inhibitor(s) in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an inhibitor(s) with the carrier and, optionally, one or more accessory ingredients. In general, the formulations are prepared by uniformly and intimately bringing into association a ligand with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouthwashes and the like, each containing a predetermined amount of an inhibitor(s) as an active ingredient. A compound may also be administered as a bolus, electuary or paste.

In solid dosage forms for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active inhibitor(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more inhibitor(s) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an inhibitor(s) include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to inhibitor(s), excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an inhibitor(s), excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The inhibitor(s) can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of an inhibitor(s) to the body. Such dosage forms can be made by dissolving or dispersing the agent in the proper medium. Absorption enhancers can also be used to increase the flux of the inhibitor(s) across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more inhibitors(s) in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of inhibitor(s) in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the inhibitors(s) of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of agents may be given orally, parenterally, topically, or rectally. They are of course given by forms suitable for each administration route. For example, they are administered in tablets or capsule form, by injection, inhalation, eye lotion, ointment, suppository, infusion; topically by lotion or ointment; and rectally by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a ligand, drug or other material other than directly into the central nervous system, such that it enters the patient's system and, thus, is subject to metabolism and other like processes, for example, subcutaneous administration.

These inhibitors(s) may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the inhibitor(s), which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

IV. EXEMPLIFICATION

The invention now being generally described, it will be more readily understood by reference to the following examples which are included merely for purposes of illustration of certain aspects and embodiments of the present invention, and are not intended to limit the invention.

Abbreviations:
EDC: N-(3-Dimethylaminopropyl)-N'-ethylcarbodiimide hydrochloride;
HOBT: 1-Hydroxybenzotriazole;
Chg: Cyclohexylglycine.

Example 1

Synthesis of Cyclohexylglycine BoroAla

Figure 1:
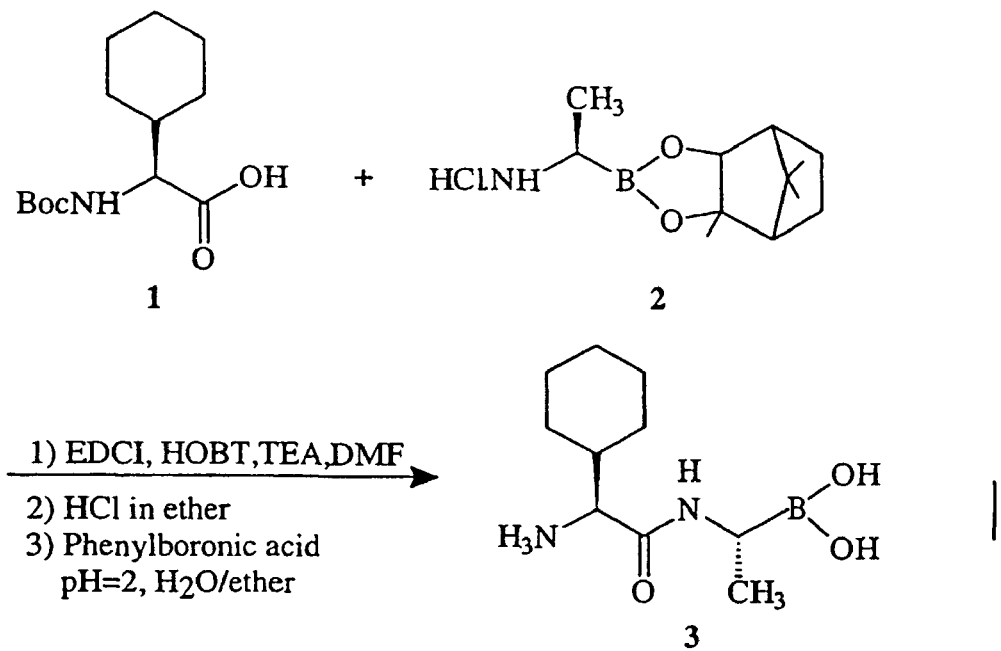
FIG. 1 is a diagrammatic representation of the synthesis of a Cyclohexylglycine-boro-Ala.

Referring to FIG. 1, a solution of 515 mg (2.00 mmol) of Boc-L-2-(cyclohexyl)glycine 1 (Chem-Impex International), 587 mg (2.26 mmol) of HCl.boroAla pinane 2, 332 mg (2.46 mmol) of HOBT, and 671 µL (4.84 mmol) of triethylamine in 6 mL of anhydrous DMF was treated with 498 mg (2.60 mmol) of EDC, and the resulting solution stirred at room temperature under argon for 18 h. The reaction mixture was diluted with a 200 mL of 10% aqueous citric acid and the resulting mixture extracted with 2×100 mL of ethyl acetate. The combined extracts were washed with brine, dried ($MgSO_4$), filtered, and concentrated to give a clear oil. The crude oil was chromatographed over silica gel with ethyl acetate/hexane to give the product ester as a clear oil. The oil was then dissolved in hydrogen chloride in diethyl ether (1.0 M solution, 25 mL) and stirred for 48 hours at room temperature. The mixture was evaporated to dryness in vacuo and redissolved in 25 mL phenylboronic acid solution (244 mg, 2 mmol) at pH 2 (0.01 N HCl) and ether (25 mL). After stirring for 30 min, the ether layer was removed and replaced with fresh ether (25 mL). This step was repeated for four times. The aqueous phase was then lyophilized and purified by HPLC to afford 170 mg (37%) of the target compound 3.

Example 2

Glucose Tolerance Test

Figure 2:
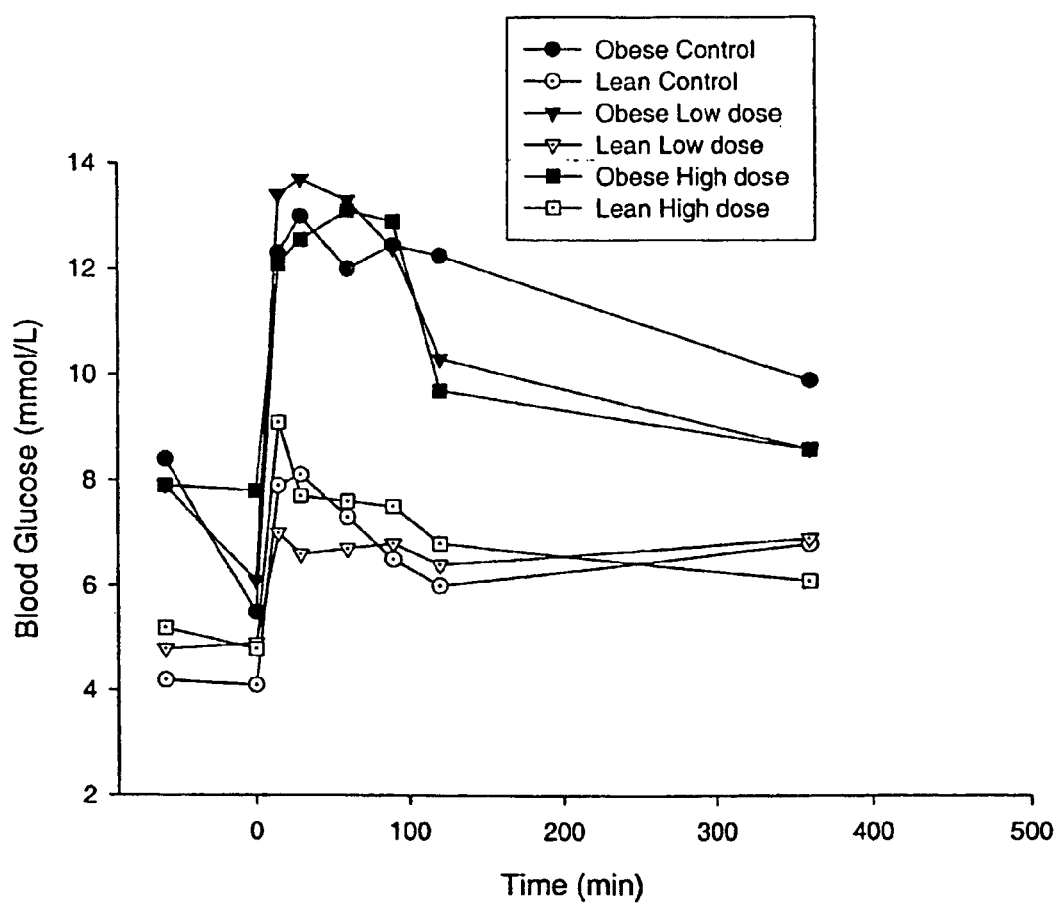
FIG. 2 is a blood glucose values curve during oral glucose challenge test in zucker rats following oral administration of Cyclohexylglycine-boro-Ala.
Figure 3:
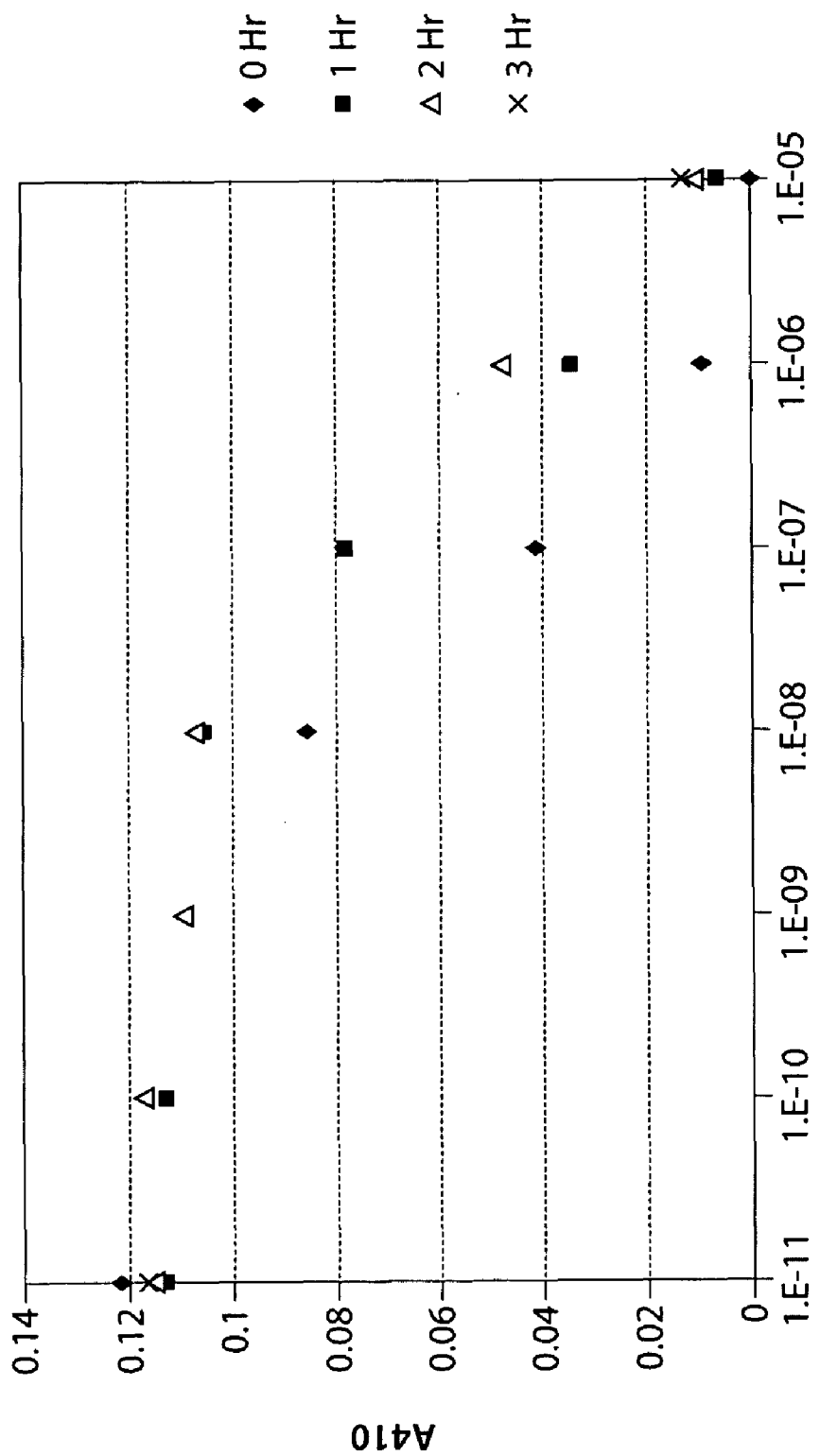
FIG. 3 is a time course of inactivation curve of His-boro-Ala at pH 8.
Figure 4:
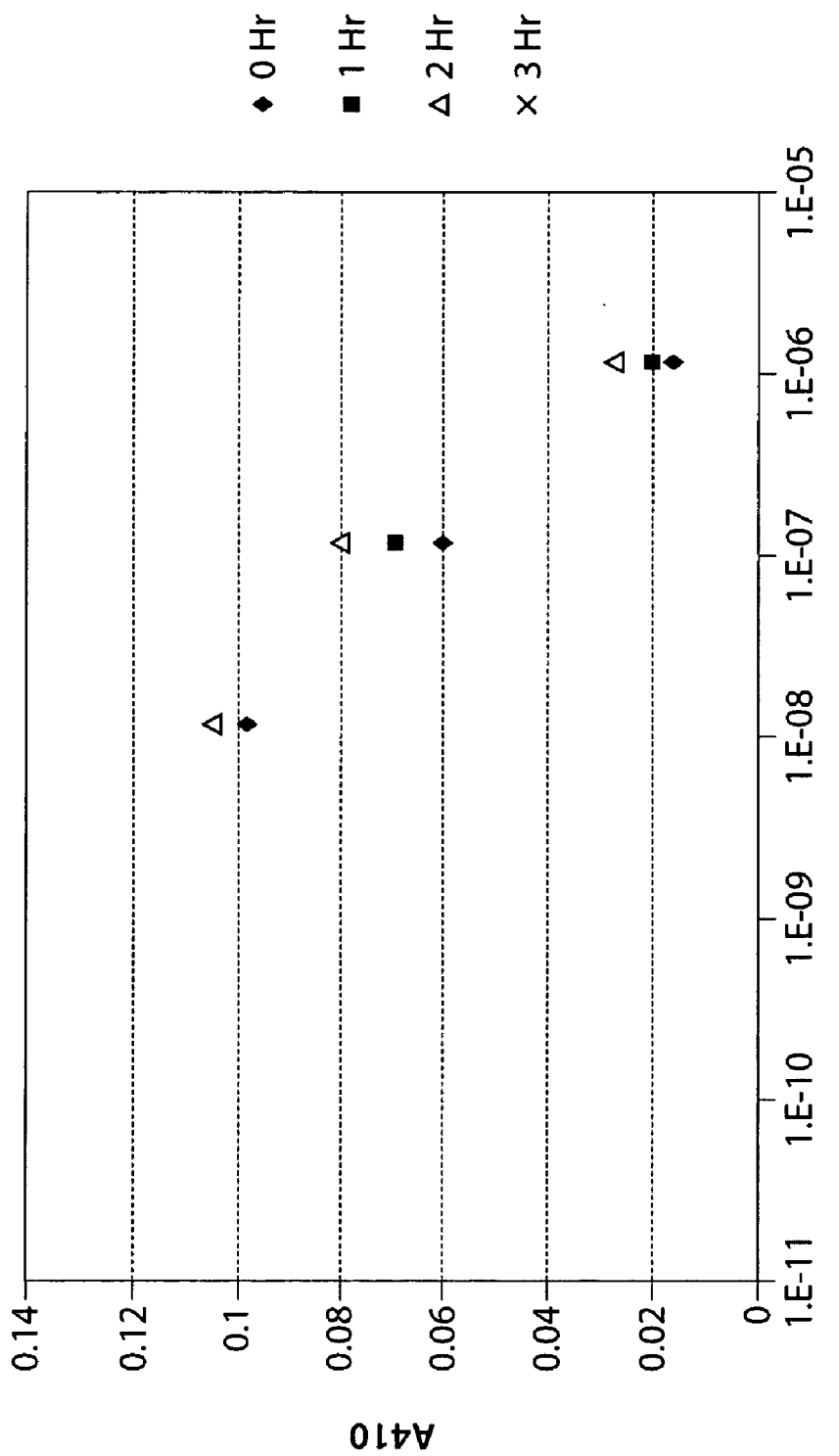
FIG. 4 is a time course of inactivation curve of Ala-boro-Ala at pH 8.
Figure 5:
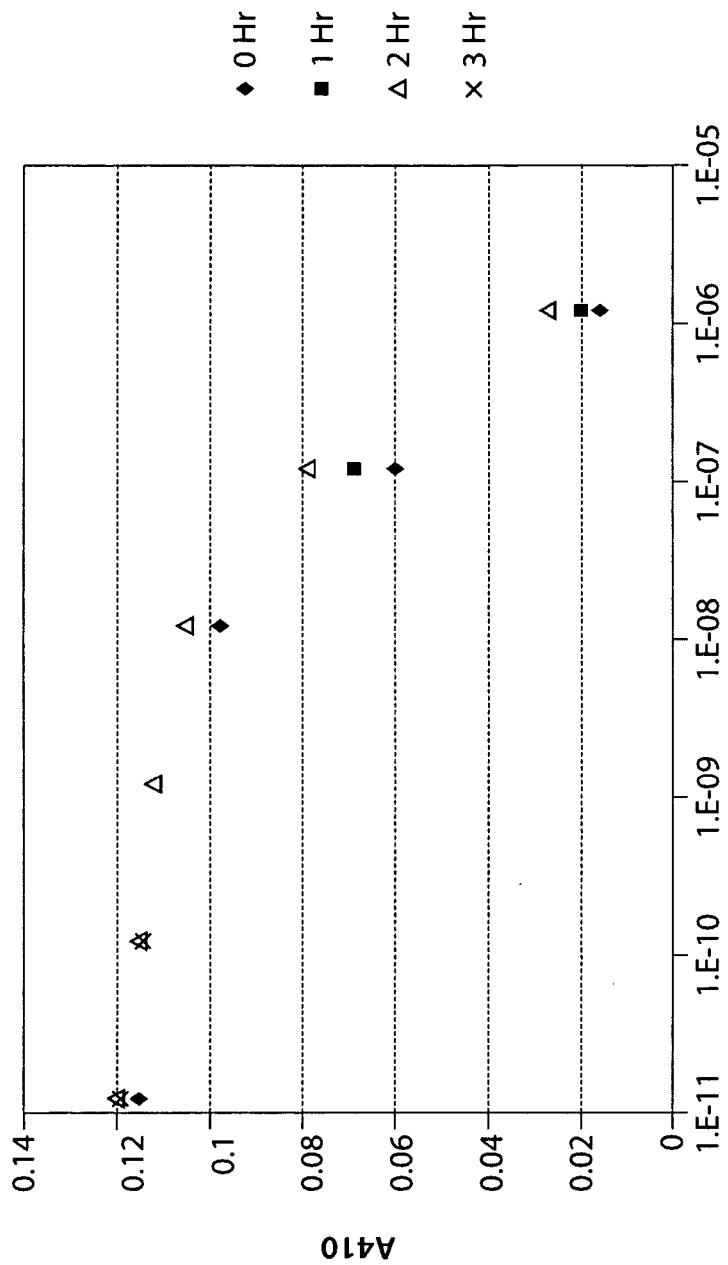
FIG. 5 is a time course of inactivation curve of Phg-boro-Ala at pH 8.
Figure 6:
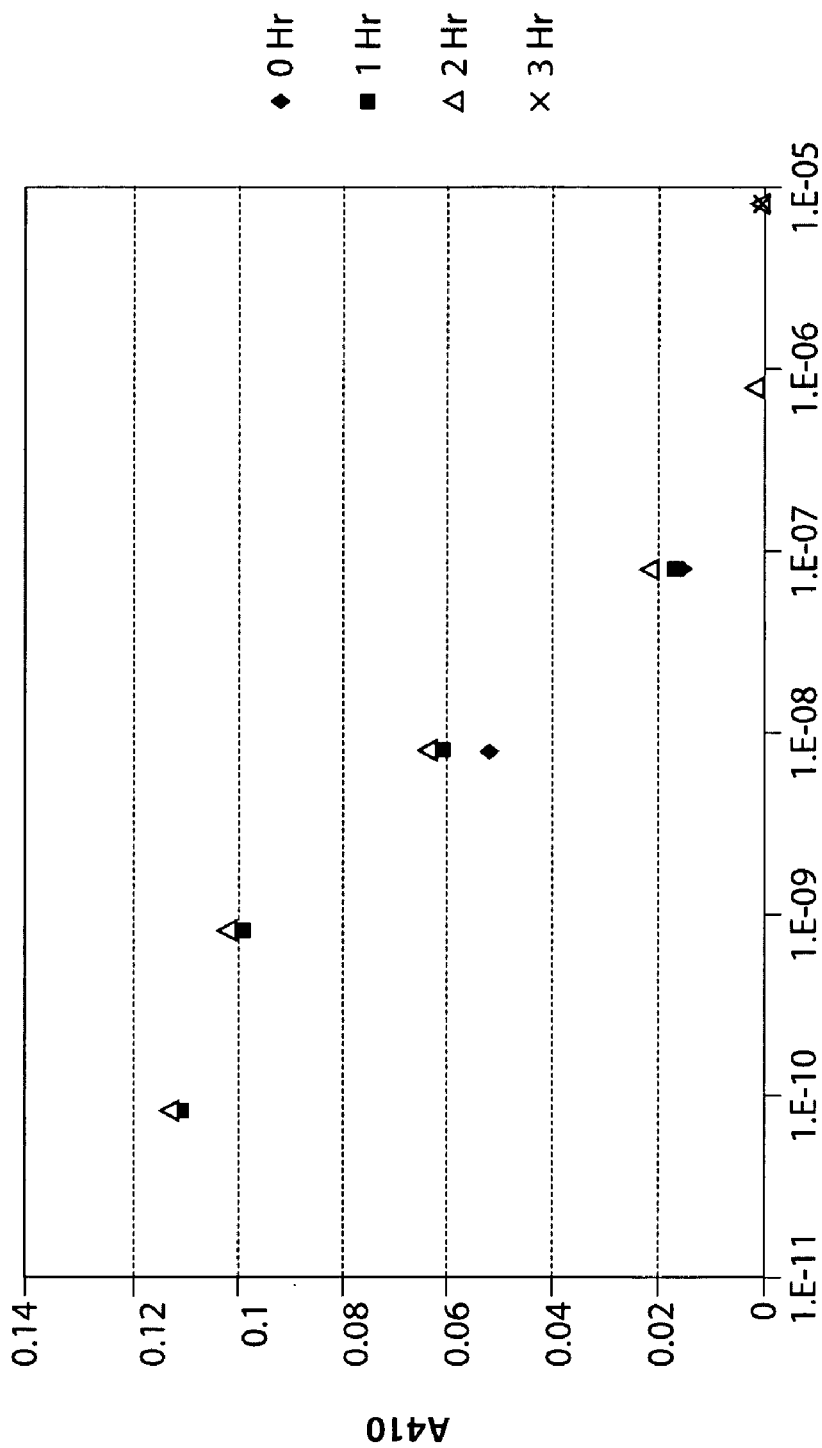
FIG. 6 is a time course of inactivation curve of Cyclohexylglycine-boro-Ala at pH 8.

Experiments show that cyclohexyl-gly boro ala is orally active and clearly lowers blood sugar based upon results from an oral glucose challenge in zucker obese rats. See FIG. 2. In these "acute" experiments zucker obese and zucker lean rats were orally administered either 0.035 mg/kg (low dose) or 0.35 mg/kg (high dose) of cyclohexyl-gly boro ala and then subjected to an oral glucose tolerance test within an hour. Each set of experiments was also performed using saline as a control.

Example 3

Inhibitor Inactivation at pH 8

Experiments show that Cyclohexylglycine-bAla does not show significant pH-time dependant inhibition as compared with His-bAla, Ala-bAla, and Phg-bAla. In this experiment stock solutions of inhibitors (His-bAla, Ala-bAla, Phg-bAla and Cyclohexylglycine-bAla) were prepared at pH 1–2. These stock solutions were pre-incubated at pH 8 as follows: first, 1:10 dilutions into a buffer (0.1 M HEPES pH 8, 0.14 M NaCl) were performed; secondly, the pH was measured after dilution and varied for different inhibitors between 7.5 and 8; and thirdly, incubations at this pH were performed for 0, 60, 120, 180 minutes. Following incubation, 1:10 serial dilutions of inhibitors in buffer and 1:10 dilution of inhibitors into Enzyme (DPPIV) in buffer were made. The inhibitors were pre-incubated with enzyme for 10 minutes to account for slow binding and substrate (H-Ala-Pro-paranitroanalide) was added at a concentration of approx.=KM (17 µM). Absorbances at 410 nm were recorded for all inhibitors after 30 minutes. See FIGS. 3–6.

Example 4

DPPIV Assays on Serum Samples from Rats

Figure 7:
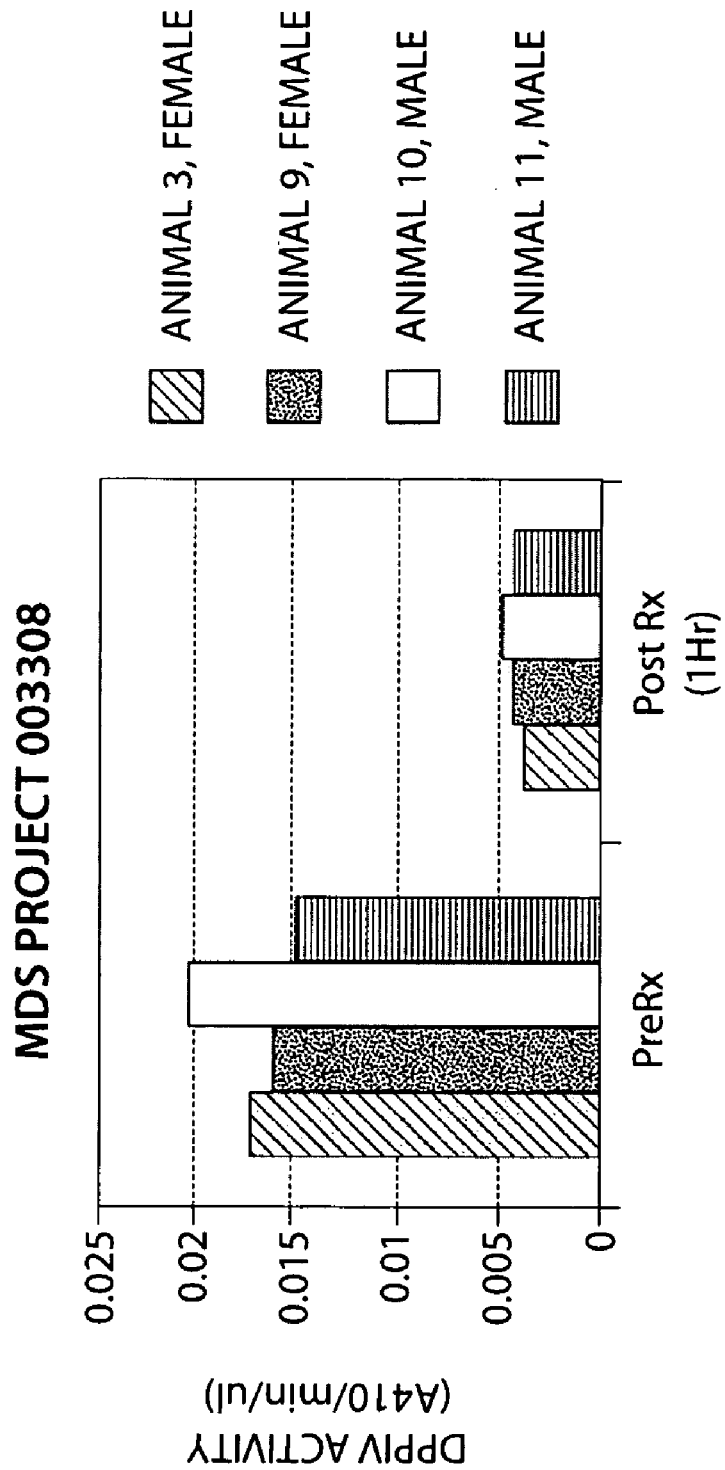
FIG. 7 is a bar graph illustrating DPPIV enzyme activity as measured from rat serum samples before and 1 hour after administration of Cyclohexylglycine-boro-Ala.

Experiments show that DPPIV enzyme activity was significantly decreased in rats treated with Cyclohexylglycine-boroAla. See FIG. 7. Four rats were used in this experiment: two females (#3 and #9) and two males (#10 and #11). Blood and plasma samples were collected from rats 1 hour after being treated with Cyclohexylglycine-boroAla. The collected serum samples were evaluated for DPPIV activity of Cyclohexylglycine-boroAla as follows:

2 mg of Ala-Pro-paranitroanalide (substrate) was dissolved in 20 ml 0.1 M HEPES pH 8, 0.14 M NaCl (buffer).

Serum samples were diluted into substrate solution in the wells of a microtiter plate. For each sample, 10 uL of serum was diluted into 150 µL of substrate.

A reading of the A410 in each well was recorded immediately after the dilution of serum into substrate, and again after approximately 1 hour. The time of data acquisition for each reading is recorded in the data file by the microplate reader software.

The rate of absorbance change was obtained by subtracting the first reading from the second and dividing by the reaction time to give DeltaA410/hr. The DPPIV activity was plotted in units of DeltaA410 hr$^{-1}$μL$^{-1}$.

Example 5

Prevention of Cyclization by Using Bulky Substituents

In this example, Xaa-boro-Ala analogs containing bulky R substituent will be constructed to prevent cyclization and increase biological activity. See FIG. 8. The inventors have previously shown that synthetic diastereomeric monomeric compounds, e.g., L-Ala-D,L-boroPro and L-Pro-D,L-boro-Pro, were potent inhibitors of the catalytic activity of soluble DPIV. They also encountered a problem because these monomeric inhibitors lost some of their inhibitory activity rapidly in aqueous solution at pH value around neutral due to a cyclization reaction. The open, active, inhibitory chain species is favored at low pH while the cyclized structure is favored at high pH. Also, the reaction is fully reversible: the open chain becomes predominate at low pH. The open chain to cyclic species reaction involves a trans to cis isomerization of the proline and the formation of a new N—B bond. The half life for the reformation of the open chain species from the cyclic structure is surprisingly slow. It has been demonstrated that the ratio of [cyclic]: [open] forms, at neutral pH, is 156:1 for Pro-boroPro and 1130:1 for Val-boroPro (W. G. Gutheil and W. W. Bachovchin, Separation of L-Pro-DL-boroPro into Its Component Diastereomers and Kinetic Analysis of Their Inhibition of Dipeptidyl Peptidase IV. A New Method for the Analysis of Slow, Tight-Binding Inhibition, Biochemistry 32, 8723–8731 (1993)). This means that less than 1% Pro-boro-Pro and less than 0.1% of Val-boroPro exists as the open chain, inhibitory species, at equilibrium at pH 7.0.

One feature of the present invention relates to the equilibrium constant for cyclization. It has been found that the ratio of [cyclic]:[open] forms for Cyclohexylglycine-boro-Ala, at neutral pH, is approximately 2:1, which is significantly lower than the corresponding ratio for Xaa-boro-Pro, as previously disclosed. In addition, the cis-trans isomerization rate, and therefore the rates of cyclization and uncyclization, are also much faster for compounds of the present invention. This feature is attributed by the inventors to a bulky substituent effect, e.g. where R in FIG. 8 represents a cyclohexyl.

Figure 8:
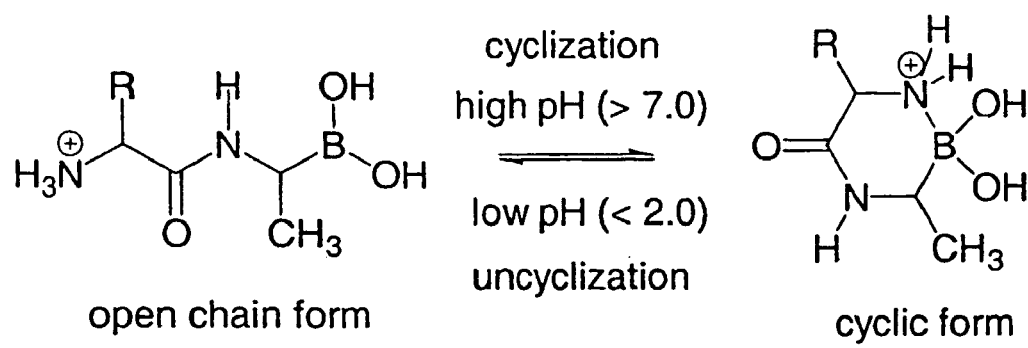
FIG. 8 is a diagrammatic representation of the conformation equilibrium of Xaa-boro-Alanine compounds.
Figure 9:
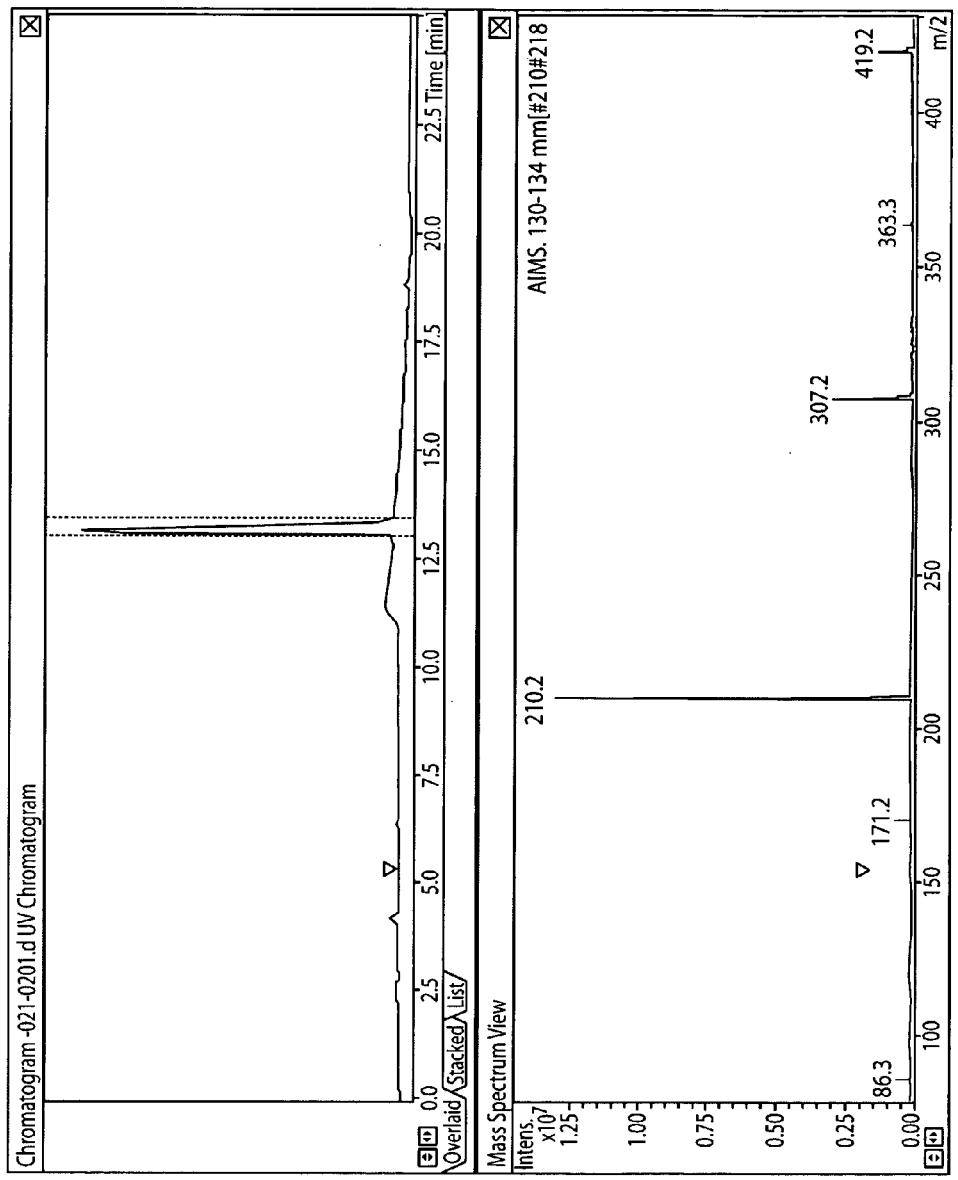
FIG. 9 is the UV chromatograph of t-Butyl-glycine-Pro-nitrile.
Figure 10:
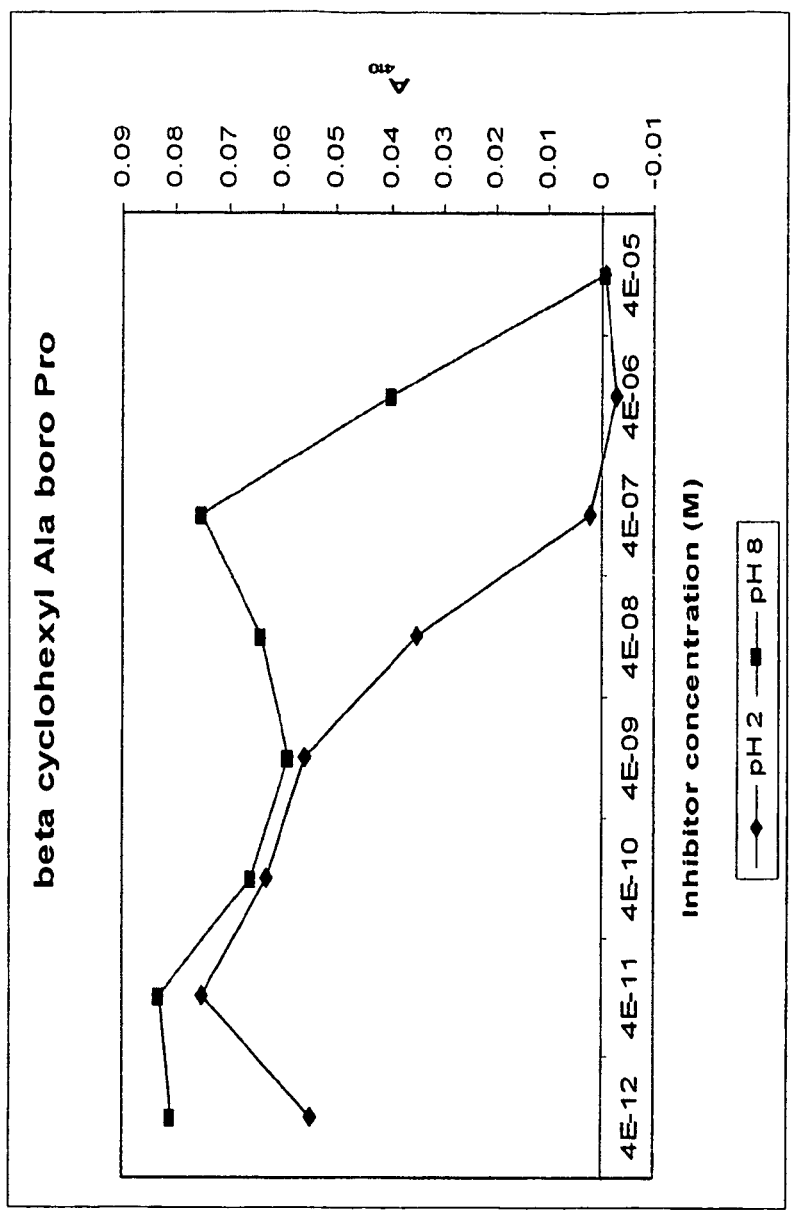
FIG. 10 is a graph showing the DPIV inhibitory activity of cyclohexylalanine-boroPro.
Figure 10:
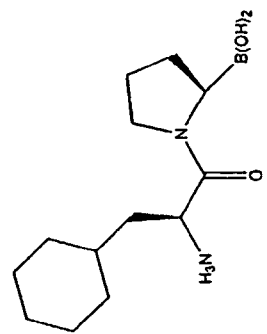

The inventors predict that biological bioavailability (biological function) for the compounds taught in this invention could be significantly increased (approximately 100–1000 times) by preventing peptide conformational changes, e.g., intramolecular cyclization, by constructing compounds bearing a variety of bulky R groups (see FIG. 8). Such compounds include but are not limited to compounds containing unnaturally occurring amino acids at P2.

IV. Equivalents

Those skilled in the art will recognize, or be able to ascertain using no more than routine experimentation, many equivalents to the specific embodiments of the invention described herein. Such equivalents are intended to be encompassed by the following claims.

All of the above-cited references and publications are hereby incorporated by reference.

What is claimed is:

1. A serine protease inhibitor represented by the following formula, or a pharmaceutically acceptable salt thereof:

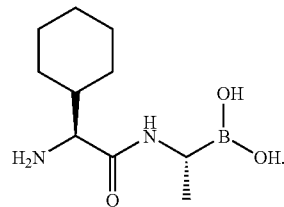

2. A pharmaceutical composition, comprising a pharmaceutically acceptable carrier; and a protease inhibitor of claim 1, or a pharmaceutically acceptable salt thereof.

3. A method for inhibiting the proteolytic activity of a post-proline cleaving enzyme, comprising contacting the enzyme with an effective amount of a protease inhibitor of claim 1.

4. The method of claim 3, wherein the inhibitor increases plasma concentrations of a peptide hormone selected from the group consisting of glucagon like peptide, NPY, PPY, secretin, GLP-1, GLP-2, and GIP.

5. A method of regulating glucose metabolism, comprising administering to a patient in need thereof a therapeutically effective amount of a protease inhibitor of claim 1.

6. The method of claim 5, wherein said patient has a glucose metabolism disorder selected from the group consisting of Type II diabetes, insulin resistance, glucose intolerance, hyperglycemia, hypoglycemia, hyperinsulinemia, obesity, hyperlipidemia, and hyperlipoproteinemia.

* * * * *